(12) United States Patent
Kawabata et al.

(10) Patent No.: US 7,842,175 B2
(45) Date of Patent: Nov. 30, 2010

(54) ELECTROPHORESIS

(75) Inventors: Tomohisa Kawabata, Tokyo (JP); Kenji Nakamura, Tokyo (JP); Shinji Satomura, Tokyo (JP)

(73) Assignee: Wako Pure Chemical Industries, Ltd., Osaka-Shi (JP)

( * ) Notice: Subject to any disclaimer, the term of this patent is extended or adjusted under 35 U.S.C. 154(b) by 2176 days.

(21) Appl. No.: 10/472,753

(22) PCT Filed: Apr. 3, 2002

(86) PCT No.: PCT/JP02/03336

§ 371 (c)(1),
(2), (4) Date: Oct. 2, 2003

(87) PCT Pub. No.: WO02/082083

PCT Pub. Date: Oct. 17, 2002

(65) Prior Publication Data

US 2004/0144649 A1 Jul. 29, 2004

(30) Foreign Application Priority Data

Apr. 4, 2001 (JP) .............................. 2001-106077

(51) Int. Cl.
*G01N 27/447* (2006.01)
(52) U.S. Cl. .................. 204/450; 204/451; 204/600; 204/601
(58) Field of Classification Search ......... 204/450–553, 204/600–650, 403; 436/161; 435/6; 210/656
See application file for complete search history.

(56) References Cited

U.S. PATENT DOCUMENTS

| | | | |
|---|---|---|---|
| 5,137,609 A | 8/1992 | Manian et al. | |
| 5,571,680 A | 11/1996 | Chen | |
| 5,591,589 A * | 1/1997 | Katoh et al. | |
| 5,605,662 A * | 2/1997 | Heller et al. | ............... 422/68.1 |
| 5,630,924 A * | 5/1997 | Fuchs et al. | |
| 5,958,202 A * | 9/1999 | Regnier et al. | .............. 204/451 |
| 5,981,171 A | 11/1999 | Kuhns | |

(Continued)

FOREIGN PATENT DOCUMENTS

EP 0 357 869 3/1990

(Continued)

OTHER PUBLICATIONS

European Patent Communication for corresponding European patent application No. 02714427, dated Sep. 16, 2004.

(Continued)

*Primary Examiner*—Kaj K Olsen
(74) *Attorney, Agent, or Firm*—Kratz, Quintos & Hanson, LLP

(57) ABSTRACT

The invention relates to a method for separating a target for measurement utilizing electrophoresis, particularly capillary electrophoresis efficiently in high sensitivity and in a short period of time. It also relates to a method for measuring said target separated by said method for separation. The invention provides a method for separating a target for measurement and a method for measuring said target separated by said method for separation, characterized by using a substance to which is bound a nucleic acid chain labeled by a marker and which has an affinity for said target for measurement.

34 Claims, 14 Drawing Sheets

U.S. PATENT DOCUMENTS

| | | | | |
|---|---|---|---|---|
| 6,027,890 | A | * | 2/2000 | Ness et al. .................... 435/6 |
| 6,103,537 | A | * | 8/2000 | Ullman et al. .............. 436/526 |
| 6,766,817 | B2 | * | 7/2004 | Da Silva |
| 7,087,148 | B1 | * | 8/2006 | Blackburn et al. .......... 205/452 |
| 2006/0141503 | A1 | * | 6/2006 | Wang ........................... 435/6 |

FOREIGN PATENT DOCUMENTS

| | | | |
|---|---|---|---|
| EP | 357869 A1 | * | 3/1990 |
| EP | 0 755 941 | | 1/1997 |
| EP | 0 815 942 | | 1/1998 |
| EP | 1 061 370 | | 12/2000 |
| JP | 7191027 | * | 7/1995 |
| JP | 1051237 T | * | 11/1998 |
| WO | WO 9606189 A1 | * | 2/1996 |

OTHER PUBLICATIONS

Andreas Manz et al., "Planar Chips Technology for Miniaturization and Integration of Separation Techniques into Monitoring Systems—Capillary Electrophoresis on a Chip", Journal of Chromatography, 593 (1992) 253-258.*

D. Jed Harrison et al., "Capillary Electrophoresis and Sample Injection Systems Integrated on a Planar Glass Chip", Anal. Chem. 1992, 64, 1926-1932.*

Stephen C. Jacobson et al., "Microchip Capillary Electrophoresis with an Integrated Postcolunm Reactor", Anal. Chem, 1994, 66, 3472-3476.*

D. Jed Harrison et al., "Micromachining a Miniaturized Capillary Electrophoresis-Based Chemical Analysis System on a Chip", Science, vol. 261, Aug. 13, 1993, 895-897.*

Carlo S. Effenhauser et al., "Glass Chips for High-Speed Capillary Electrophoresis Separations with Submicrometer Plate Heights", Anal. Chem. 1993, 65, 2637-2642.*

Adam T. Woolley et al., "Ultra-High-Speed DNA Fragment Separations Using Microfabricated Capillary Array Electrophoresis Chips", Proc. Natl. Acad. Sci. USA, vol. 91, pp. 11348-11352, Nov. 1994.*

Stephen C. Jacobson et al., "Integrated Microdevice for DNA Restriction Fragment Analysis", Anal. Chem. 1996, 68, 720-723.*

Adam T. Woolley et al., "High-Speed DNA Genotyping Using Microfabricated Capillary Array Electrophoresis Chips", Anal. Chem. 1997, 69, 2181-2186.*

Carlo S. Effenhauser et al., "High-Speed Separation of Antisense Oligonucleotides on a Micromachined Capillary Electrophoresis Device", Anal. Chem. 1994, 66, 2949-2953.*

Adam T. Woolley et al., "Ultra-High-Speed DNA Sequencing Using Capillary Electrophoresis Chips", Anal. Chem. 1995, 67, 3676-3680.*

Shao Yao et al., "SDS Capillary Gel Electrophoresis of Proteins in Microfabricated Channels", Proc. Natl. Acad. Sci. USA, vol. 96, pp. 5372-5377, May 1999.*

* cited by examiner

Introduction of the Sample          Separation of the Sample

Introduction of the Sample    Separation of the Sample

ELECTROPHORESIS

This application is a national stage application under 35 U.S.C. 371 of PCT/JP02/03336, filed Apr. 3, 2002.

TECHNICAL FIELD

The present invention relates to a method for separating substances utilizing electrophoresis and a method for measuring the target for measurement separated by said method for separation.

BACKGROUND ART

In a Micro Total Analysis System (μ-TAS; Laboratory on a chip), which is assumed a means for analysis of the next generation, a series of chemical and biochemical analyses such as extraction of a target component for analysis from a biological sample (extraction step), analyses of the component using a chemical/biochemical reaction (analytical step), as well as subsequent processing for separation (separation step) and detection (detection step), all are conducted on a extremely small analyzer integrated on a chip, several cm to several ten cm on one side. As for the separating methods for this system, the following methods have widely been noticed. Capillary electrophoresis utilizes a difference of the charge of substances in a high electric field, in which a capillary (fine tube), 1 mm or less in the inside diameter, is prepared with a polymer compound, Teflon or silica as a material easily applicable on a substrate by fine processing. Capillary column chromatography utilizes a difference of the interaction between a column carrier and a substance, using a similar capillary.

Among them, the capillary electrophoresis has characteristics that since the capillary surface area is considerably large relative to the capillary inside volume, generation of the Joule heat by application of high voltage is efficiently blocked and it gives higher resolution in a short period of time than the conventional electrophoresis. Therefore, the capillary electrophoresis has been considered as a method suitable for μ-TAS since the separation is allowed in a relatively short length for separation.

Particularly, recent years, a technique for separation, a so-called capillary chip electrophoresis has been develop as one of capillary electrophoretic methods used for μ-TAS, in which a capillary is made on a chip several cm to several ten cm on one side by means of a fine processing technique such as photolithography. [J. Chromatogr. (1992) 593, 253-258, Manz, A. et al., Anal. Chem. (1992) 64, 1926-1932, Harrison, D. J. et al., Anal. Chem. (1994) 66, 3472-3476, Jacobson, S. C. et al., Science (1993) 261, 895-897, Harrison, D. J. et al., Anal. Chem. (1993) 65, 2637-2642, Effenhauser, C. S. et al. and so on]

In the above-mentioned capillary chip electro-phoretic method, however, there is a limitation in the length of capillary for separation, and the length for separation is extremely shortened in comparison with that of conventional capillary electrophoresis. Therefore, it becomes an issue that separability for relatively large molecules such as nucleic acids, polypeptides, proteins, etc., is insufficient, though it is sufficient for low molecular substances greatly influenced by an intramolecular electric charge.

In order to solve this issue, a method for separation using a polymer having molecular sieve effect, for example, hydroxyethylcellulose, polyacrylamide, and the like, as an additive added into the capillary has been developed. [Proc. Natl. Acad. Sci. USA (1994) 91, 11348-11352, Woolly, A. T. and Mathies, R. A., Anal. Chem. (1996) 68, 720-723, Jacobson, S. C. and Ramsey, J. M., Anal. Chem. (1997) 69, 2181-2186, Woolley, A. T., et al., Proc. Natl. Acad. Sci. USA (1994) 91, 11348-11352, Woolley, A. T. and Mathies, R. A., Anal. Chem. (1994) 66, 2949-2953, Effenhauser, C. S., et al., Anal. Chem (1995) 67, 3676-3680, and so on]. In the existing circumstance, however, separation of polypeptides or proteins is still insufficient even according to these methods.

It is also proposed as another method for separating proteins by using an acrylamide polymer having a molecular sieve effect as a capillary-packing agent in the presence of sodium dodecylsulfate [SDS-PAGE: Proc. Natl. Acad. Sci. USA (1999) 96, 5372-5377, Yao, S., et al., and so on]. In this method, however, since the proteins have to be denatured with sodium dodecylsulfate, it is difficult to separate them while keeping their own activities such as specific binding activity.

In order to solve these problems, the following method has been reported (Japanese Patent No. 3,070,418; International Patent Publication No. 512371/1998). A target component for analysis is allowed to react with 2 species of substances, one which has a specific affinity to the target and binds to a charged substance and another which has a specific affinity to the target and binds to a detectable marker, to form a complex comprising these 3 components (substance which has a specific affinity to the target and binds to a charged substance—target component for analysis—substance which has a specific affinity to the target and binds to a detectable marker). The complex is separated from the substance which has a specific affinity to the target and binds to a detectable marker not involved in the formation of the complex, by an electrically (B/F) separating method utilizing the difference of the charge between the charged substance contained in the complex and the substance which has a specific affinity to the target and binds to a detectable marker not involved in the formation of the complex.

In this method, however, it is necessary that the charged substance improving separation ability and the marker for detection each has been always bound to a different type of substance which has a specific affinity to the target. As an additional disadvantage, it is also necessary to adjust the amount of the detectable marker which is bound to a substance capable of specifically binding to the target component, since the charge of the substance capable of specifically binding to the target component and binding to the detectable marker is changed to decrease the separation accuracy and broaden the separation peak.

In view of the above-mentioned state, the invention intends to provide a method for separating a target for measurement utilizing electrophoresis efficiently in high sensitivity and in a short period of time and a method for measuring the target for measurement separated by the method for separation.

DISCLOSURE OF INVENTION

The invention was made to solve the above-mentioned problems and relates to the followings.

(1) A method for separation of a target for measurement which comprises using a substance to which is bound a nucleic acid chain labeled with a marker and which has an affinity for said target for measurement.

(2) A method for separation by electrophoresis which comprises forming a complex comprising the target for measurement—(the nucleic acid chain-binding affinity substance-marker) from a sample containing a target for measurement, a substance to which is bound a nucleic acid chain and which has an affinity to the target for measurement (hereinafter sometimes abbreviated to as nucleic acid chain-binding affinity substance), and a marker capable of labeling said nucleic acid chain, and separating said complex from the nucleic acid chain-binding affinity substance-marker not involved in the formation of said complex and if required from the marker by electrophoresis.

(3) A method for separation by electrophoresis which comprises mutually contacting a sample containing a target for measurement, a substance to which is bound a nucleic acid chain and which has an affinity to the target for measurement (nucleic acid chain-binding affinity substance), and a marker capable of labeling said nucleic acid chain, and separating the resulting complex comprising the target for measurement—(the nucleic acid chain-binding affinity substance-marker) from the nucleic acid chain-binding affinity substance-marker not involved in the formation of said complex and if required from the marker by electrophoresis.

(4) A method for separation by electrophoresis which comprises forming a complex comprising the target for measurement—(two or more species of the nucleic acid chain-binding affinity substance-marker) from a sample containing a target for measurement, two or more species of substances to which is bound a nucleic acid chain and which have an affinity to the target for measurement and mutually different binding sites for the target for measurement, and a marker capable of labeling said nucleic acid chain, and separating said complex from the nucleic acid chain-binding affinity substance-marker not involved in the formation of said complex and if required from the marker by electrophoresis.

(5) A method for separation by electrophoresis which comprises mutually contacting a sample containing a target for measurement, two or more species of substances to which is bound a nucleic acid chain and which have an affinity to the target for measurement and mutually different binding sites for the target for measurement, and a marker capable of labeling said nucleic acid chain, and separating the resulting complex comprising the target for measurement—(two or more species of the nucleic acid chain-binding affinity substance-marker) from the nucleic acid chain-binding affinity substance-marker not involved in the formation of said complex and if required from the marker by electrophoresis.

(6) A method for separation by electrophoresis which comprises forming [1] a complex of the target $A_1$ for measurement—nucleic acid chain-binding affinity substance $B_{A1:An}$—marker, [2] a complex of the target $A_2$ for measurement—nucleic acid chain-binding affinity substance $B_{A1:An}$ and nucleic acid chain-binding affinity substance $B_{A2:An}$—marker, [3] a complex of the target $A_3$ for measurement—nucleic acid chain-binding affinity substance $B_{A1:An}$, nucleic acid chain-binding affinity substance $B_{A2:An}$ and nucleic acid chain-binding affinity substance $B_{A3:An}$—marker, . . . , [n−1] a complex of the target $A_{n-1}$ for measurement—nucleic acid chain-binding affinity substance $B_{A1:An}$, nucleic acid chain-binding affinity substance $B_{A2:An}$, nucleic acid chain-binding affinity substance $B_{A3:An}$, . . . and nucleic acid chain-binding affinity substance $B_{An-1:An}$—marker, and [n] a complex of the target $A_n$-nucleic acid chain-binding affinity substance $B_{A1:An}$, nucleic acid chain-binding affinity substance $B_{A2:An}$, nucleic acid chain-binding affinity substance $B_{A3:An}$, . . . nucleic acid chain-binding affinity substance $B_{An-1:An}$ and nucleic acid chain-binding affinity substance $B_{An}$—marker from (a) a sample containing mutually different n types of targets $A_1, A_2, A_3, \ldots A_{n-1}$ and $A_n$ for measurement, (b)(1) a substance to which is bound a nucleic acid chain and which has an affinity to all of the targets $A_1$ to $A_n$ for measurement (nucleic acid chain-binding affinity substance $B_{A1:An}$), (2) a substance to which is bound a nucleic acid chain and which has an affinity to all of the targets $A_2$ to $A_n$ for measurement except for $A_1$ (nucleic acid chain-binding affinity substance $B_{A2:An}$), (3) a substance to which is bound a nucleic acid chain and which has an affinity to all of the targets $A_3$ to $A_n$ for measurement except for $A_1$ and $A_2$ (nucleic acid chain-binding affinity substance $B_{A3:An}$), . . . , (n−1) a substance to which is bound a nucleic acid chain and which has an affinity to the targets $A_{n-1}$ and $A_n$ for measurement except for all of $A_1$ to $A_{n-2}$ (nucleic acid chain-binding affinity substance $B_{An-1:An}$) and (n) a substance to which is bound a nucleic acid chain and which has an affinity only to the target $A_n$ for measurement except for all of $A_1$ to $A_{n-1}$ (nucleic acid chain-binding affinity substance $B_{An}$), and (c) a marker capable of labeling said nucleic acid chain, and then separating the respective complexes [1] to [n] from complexes of the respective nucleic acid chain-binding affinity substances (1) to (n) and the markers not involved in the formation of said complexes and if required from the markers by electrophoresis.

(7) A method for separation by electrophoresis which comprises mutually contacting (a) a sample containing mutually different n types of targets $A_1, A_2, A_3, \ldots A_{n-1}$ and $A_n$ for measurement, (b)(1) a substance to which is bound a nucleic acid chain and which has an affinity to all of the targets $A_1$ to $A_n$ for measurement (nucleic acid chain-binding affinity substance $B_{A1:An}$), (2) a substance to which is bound a nucleic acid chain and which has an affinity to all of the targets $A_2$ to $A_n$ for measurement except for $A_1$ (nucleic acid chain-binding affinity substance $B_{A2:An}$), (3) a substance to which is bound a nucleic acid chain and which has an affinity to all of the targets $A_3$ to $A_n$ for measurement except for $A_1$ and $A_2$ (nucleic acid chain-binding affinity substance $B_{A3:An}$), . . . , (n−1) a substance to which is bound a nucleic acid chain and which has an affinity to the targets $A_{n-1}$ and $A_n$ for measurement except for all of $A_1$ to $A_{n-2}$ (nucleic acid chain-binding affinity substance $B_{An-1:An}$), and (n) a substance to which is bound a nucleic acid chain and which has an affinity only to the target $A_n$ for measurement except for all of $A_1$ to $A_{n-1}$ (nucleic acid chain-binding affinity substance $B_{An}$), and (c) a marker capable of labeling said nucleic acid chain, and separating the resulting [1] a complex of the target $A_1$ for measurement—nucleic acid chain-binding affinity substance $B_{A1:An}$—marker, [2] a complex of the target $A_2$ for measurement—nucleic acid chain-binding affinity substance $B_{A1:An}$ and nucleic acid chain-binding affinity substance $B_{A2:An}$—marker, [3] a complex of the target $A_3$ for measurement—nucleic acid chain-binding affinity substance $B_{A1:An}$, nucleic acid chain-binding affinity substance $B_{A2:An}$ and nucleic acid chain-binding affinity substance $B_{A3:An}$—marker, . . . , [n−1] a complex of the target $A_{n-1}$ for measurement—nucleic acid chain-binding affinity substance $B_{A1:An}$, nucleic acid chain-binding affinity substance $B_{A2:An}$, nucleic acid chain-binding affinity substance $B_{A3:An}$, . . . and nucleic acid chain-binding affinity substance $B_{An-1:An}$—marker, and [n] a complex of the target $A_n$ for measurement—nucleic acid chain-binding affinity substance $B_{A1:An}$, nucleic acid chain-binding affinity substance $B_{A2:An}$, nucleic acid chain-binding affinity substance $B_{A3:An}$, . . . nucleic acid chain-binding affinity substance $B_{A2:An}$ and nucleic acid chain-binding affinity substance $B_{An}$—marker from complexes of the respective nucleic acid chain-binding affinity substances (1) to (n) and the markers not involved in the formation of said complexes and if required from the markers by electrophoresis.

(8) A method for separation by electrophoresis which comprises forming 2 or more species of complexes comprising specific targets for measurement—nucleic acid chain-binding substances having an affinity only for said specific targets for measurement—marker from a sample containing 2 or more types of targets for measurement, 2 or more species of substances to which is bound a nucleic acid chain and which have an affinity only for one of the targets for measurement (hereinafter sometimes abbreviated to as specific nucleic acid chain-binding affinity substances), and a marker capable of labeling said nucleic acid chain, and then separating said complexes from the specific nucleic acid chain-binding affinity substance-marker not involved in the formation of said complexes and if required from the marker respectively by electrophoresis.

(9) A method for separation by electrophoresis which comprises mutually contacting a sample containing 2 or more types of targets for measurement, 2 or more species of substances to which is bound a nucleic acid chain and which have an affinity only for any one of the intended targets for measurement (specific nucleic acid chain-binding affinity substances), and a marker capable of labeling said nucleic acid chain, and separating the resulting 2 or more species of complexes comprising specific targets for measurement—nucleic acid chain-binding substances having an affinity only for said specific targets for measurement—marker from the specific nucleic acid chain-binding affinity substance-marker not involved in the formation of said complexes and if required from the marker respectively by electrophoresis.

(10) A kit for measuring a target utilizing electrophoresis, comprising a substance to which is bound a nucleic acid chain and which have an affinity for the target for measurement and a marker capable of labeling said nucleic acid chain.

(11) A kit for measuring a target utilizing electrophoresis, comprising a substance which has an affinity for the target for measurement and to which is bound a nucleic acid chain labeled by a marker.

The present inventors worked assiduously to study searching for a method of separating a target for measurement efficiently in high sensitivity in a short period of time utilizing electrophoresis, particularly capillary electrophoresis. As a result, they have found that when a target for measurement, a substance to which is bound a nucleic acid chain and which has an affinity for the target for measurement, and a marker are formed into a complex of the target for measurement—the substance to which is bound a nucleic acid chain and which has an affinity for the target for measurement—the marker, said complex, i.e., the complex containing the target for measurement, can be separated efficiently in a short period of time, and additionally the target for measurement in a sample can be measured in high sensitivity in a short period of time, and further the detection sensitivity can freely be controlled. Thus, the invention was completed.

BEST MODE FOR CARRYING OUT THE INVENTION

Figure 1:
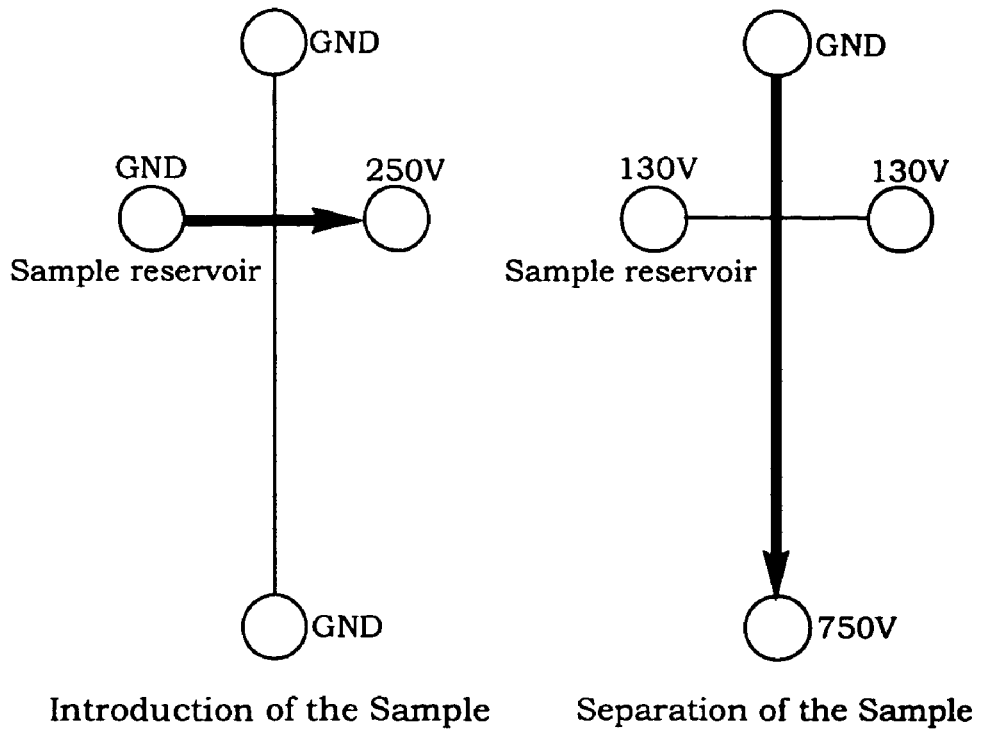
FIG. 1 shows schematically the principle and an apparatus of capillary electrophoresis.

The method for separation of a target for measurement in the invention is characterized by using a substance which has an affinity for the target for measurement and to which is bound a nucleic acid chain labeled with a marker.

In other words, a target for measurement is finally converted, using a substance which has an affinity for the target for measurement and to which is bound a nucleic acid chain labeled with a marker, into a complex comprising the target, the substance which has an affinity for the target for measurement and to which is bound a nucleic acid chain (nucleic acid chain-binding affinity substance), and the marker capable of labeling the nucleic acid chain. More specifically, a complex [target for measurement—(nucleic acid chain-binding affinity substance-marker) complex] comprising (a) a target for measurement, (b) a substance which has an affinity for the target for measurement and to which is bound a nucleic acid chain (nucleic acid chain-binding affinity substance) and a marker capable of labeling the nucleic acid chain, is finally formed. This complex is then separated from the nucleic acid chain-binding affinity substance-marker, and if required from the marker.

The nucleic acid chain used in the invention has nucleotide residues as basic units comprising purine bases or pyrimidine bases, pentose as sugar portion, and phosphates. The respective nucleotides are linking and polymerizing at the 3' and 5' carbons of the sugar potion through the diester bond of the phosphates to form a polynucleotide chain, for example, RNA in which the sugar portion is ribose and/or DNA in which the sugar portion is deoxyribose. The nucleic acid chain may be of single strand, double strand, or more.

The nucleic acid chain used in the invention may be prepared in a per se conventional manner, for example, chemical synthesis, a method for extraction and purification of the nucleic acid chain from the cells derived from microorganisms, insects, animals, plants, etc., a method using the above-mentioned cells into which has been introduced a suitable vector gene such as plasmid, phage, cosmid, etc., in which method the cells are cultivated and the multiplied vector is extracted and purified, and a method utilizing a gene-amplification technique such as PCR (Molecular Cloning, A Laboratory Mannual, 2nd Edition, J. Sambrook, E. F. Fritsch, T. Maniatis, Cold Spring Harbor Laboratory Press, etc.). Thus resulting nucleic acid chain is cleaved by chemical decomposition or with a nucleic acid-cleavage enzyme such as restriction enzymes and then optionally purified to form a nucleic acid chain of the desired length.

The length of the used nucleic acid chain may be usually 1 bp to 1,000 kbp, preferably 5 bp to 100 kbp, more preferably 10 bp to 50 kbp, as far as the purpose of the invention can be attained.

The nucleic acid chain used in the invention may be modified properly with a suitable one within the scope of attaining the purpose of the invention.

The substance having an affinity for the target for measurement used in the invention includes, for example, those having a property capable of binding to the target for measurement depending on the interaction between proteins, between protein and chemical substance, or between chemical substances. Specifically, those binding based on the interaction between "antigen" and "antibody", "sugar chain" and "lectin", "enzyme" and "inhibitor", "protein" and "peptide chain", or "receptor" and "ligand" are included. When one of the substances in the above-mentioned pairs is the target for measurement, the other is the substance having an affinity for the target for measurement. For example, when the target for measurement is an antigen, the substance having an affinity for the target for measurement is an antibody, and when the target for measurement is an antibody, the substance having an affinity for the target for measurement is an antigen (the same applied to the above other pairs).

More specifically, such a substance includes, for example, peptide chains (e.g., C-peptide, angiotensin I, etc.), proteins (e.g., immunoglobulin A (IgA), immunoglobulin E (IgE), immunoglobulin G (IgG), immunoglobulin M (IgM), immunoglobulin D (IgD), $\beta_2$-microglobulin, albumin, their degradation products, serum proteins such as ferritin, enzyme proteins such as amylase, alkaline phosphatase, γ-glutamyltransferase, etc.; proteins or peptides or glycosyl antigens derived from microorganisms, bacteria such as tubercule bacillus, pneumococci, *Corynebacterium diphteriae, Neisseria meningitidis*, gonococci, staphylococci, streptococci, intestinal bacteria, *Escherichia coli, Helicobacter pylori*, etc., viruses such as Rubella virus, Herpes virus, Hepatitis viruses, ATL virus, AIDS virus, influenzavirus, adenovirus, enterovirus, poliovirus, EB virus, HAV, HBV, HCV, HIV, HTLV, etc., fungi such as Candida, Cryptococcus, etc., spirochaete such as leptospira, *Treponema pallidum*, etc., chlamydia, mycoplasma, and the like; a variety of allergens causing allergies such as asthma, allergic rhinitis, atopic dermatitis, etc., which are derived from, for example, house dust, mites such as *Dermatophagoides farinae, Dermatophagoides pteronyssinus*, etc., pollen of Japanese cedar, Japanese cypress, Pasplum, common ragweed, *Phleum pratense, Anthoxanthum odoratum*, rye, etc., animals such as cat, dog, crab, etc., food such as rice, albumen, etc., fungi, insects, wood, drugs, chemicals, and the like; lipids such as lipoproteins, etc., proteases such as trypsin, plasmin, serine protease, etc., tumor marker protein antigens such as AFP, PSA, CEA, PGI, PGII, etc., sugar chains (e.g., tumor marker glycosyl (carbohydrate) antigen sugar chain such as CA19-9, PIVKA-II, CA125, sugar chain possessed by a substance containing a special sugar chain produced by cancer cells, e.g., ABO glycosyl antigen, etc.), lectin (e.g., concanavalin A, lectin of *Lens esculenta*, lectin of *Phaseolus vulgaris*, stramonium lectin, wheat germ lectin, etc.), phospholipids (e.g., cardiolipin, etc.), lipopolysaccharides (e.g., endotoxin, etc.), chemical substances (for example, hormones such as PTH, T3, T4, TSH, insulin, LH, FSH, prolactin, etc., environmental hormones such as tributyltin, nonylphenol, 4-octyl-phenol, di-n-butyl phthalate, dicyclohexyl phthalate, benzophenone, octachlorostyrene, di-2-ethylhexyl phthalate, etc.), receptors (e.g., receptors for estrogen, THS, etc.), ligands (e.g., estrogen, TSH, etc.), and antibodies thereto. In this connection, the antibodies used in the invention also include Fab or F(ab')$_2$ fragments as degradation products produced by degradation with a proteolytic enzyme (proteinase) such as papain or pepsin or by chemical degradation.

In the invention, the binding of a nucleic acid chain to a substance having an affinity for the target for measurement may be carried out utilizing the respective functional groups of the substance having an affinity for the target for measurement and of the nucleic acid chain directly or through a linker [for example, sulfo-succinimidyl 4-(p-maleimidophenyl)butyrate (Sulfo-SMPB), sulfosuccinimidyl 4-(N-maleimidomethyl)cyclo-hexane-1-carboxylate (Sulfo-SMCC), N-(ε-maleimido-caproyloxy)succinimide (EMCS), etc.]. The binding may be conducted in a conventional manner usually used in this field, for example, per se known labeling method utilized in per se known EIA, RIA, FIA or hybridization [for example, Ikagaku Jikken Koza (Experimental Manual in Medical Chemistry), vol. 8, Edited by Yuichi Yamamura, First edition, Nakayama Shoten, 1971; Zusetu (Illustrative Description) Fluorescent Antibodies, Akira Kawao, First Edition, Soft Science, 1983; Enzyme Immunoassay, Eiji Ishikawa, Tadashi Kawai, Kiyoshi Miyai, 3rd Edition, Igaku-Shoin, 1987; Molecular Cloning, A Laboratory Mannual, 2nd Edition, J. Sambrook, E. F. Fritsch, T. Maniatis, Cold Spring Harbor Laboratory Press, etc.] or in a conventional method utilizing the reaction of avidin (or streptavidin) with biotin.

After preliminary introduction of a reactive functional group to the nucleic acid chain, the substance having an affinity for the target for measurement may be linked to the nucleic acid chain introduced the reactive functional group in the above-mentioned binding method. The introduction of a reactive functional group into the nucleic acid chain may be conducted according to a per se known method including, for example, a method for introducing a reactive functional group by linking the 5' triphosphate group located at the terminal of the nucleic acid with a compound having a reactive functional group (e.g., a compound having an amino group such as N-trifluoroacetylaminoalkylamine, a compound having a thiol group such as cystamine, a compound having biotin such as N-biotinylaminoalkylamine, a compound having a maleimido group such as maleimidoalkylamine, etc.) in formation of a phosphoamidite bond using a condensing agent, e.g., 1-ethyl-3-(3-dimethyl-aminopropyl)carbodiimide hydrochloride (WSC), etc. [Nucleic Acid Res. (1988) 16, 3671, Chu, B. C., et al.]; a method for introducing a reactive functional group by linking the 3' hydroxyl group located at the terminal of the nucleic acid with a compound having a reactive functional group (e.g., a compound having an amino group such as N-trifluoroacetylaminoalkylcarboxylic acid, a compound having biotin such as N-biotinylaminoalkylcarboxylic acid, a compound having a maleimido group such as maleimidoalkylcarboxylic acid, etc.) in formation of an ester bond using a condensing agent, e.g., 1-ethyl-3-(3-dimethylaminopropyl)carbodiimide hydrochloride (WSC), etc., or by reacting the 3' hydroxy group with active esters of the compound having a reactive functional group directly [Nucleic Acid Res. (1986) 14, 6115, Jabloski, et al.); a method for introduction of an amino-reactive linker into a restriction enzyme-cleaved fragment at the terminal from which an amino-containing base (adenine, cytosine) is protruded as a single strand [Chemistry of Proteins and Crosslinking, Shan S. Wong, (1991) Published by CRC Press]; a method for incorporation of a nucleotide monomer having a reactive functional group in a restriction enzyme-cleaved fragment forming a single strand-protruded end with a blunting enzyme (T4 DNA polymerase, DNA blunting enzyme, etc.) (Molecular Cloning, A Laboratory Mannual, 2nd Edition, J. Sambrook, E. F. Fritsch, T. Maniatis, Cold Spring Harbor Laboratory Press, etc.); a method for utilizing hybridization, wherein a reactive functional group is introduced into the 5' end of an oligonucleotide having a complimentary sequence for the single stranded portion of a restriction enzyme-cleaved fragment forming a single strand-protruded end to hybridize at the single strand-protruded end of the restriction enzyme-cleaved fragment (Molecular Cloning, A Laboratory Mannual, 2nd Edition, J. Sambrook, E. F. Fritsch, T. Maniatis, Cold Spring Harbor Laboratory Press, etc.); a method utilizing PCR, wherein a PCR primer into which a reactive functional group has been introduced at the 5' end is used in PCR to yield as a PCR product a nucleic acid chain into which a reactive functional group has been introduced at the 5' end (Molecular Cloning, A Laboratory Mannual, 2nd Edition, J. Sambrook, E. F. Fritsch, T. Maniatis, Cold Spring Harbor Laboratory Press, etc.). Thus, a reactive functional group can be introduced into the terminal of nucleic acids. When a single strand nucleic acid is used, the nucleic acid chain into which a reactive functional group has been introduced may also be prepared according to a method for hybridizing to the single strand nucleic acid an oligonucleotide having a sequence complimentary to the 5' end of the nucleic acid chain and a reactive functional group introduced at 5' end (Molecular Cloning, A Laboratory Mannual, 2nd Edition, J. Sambrook, E. F. Fritsch, T. Maniatis, Cold Spring Harbor Laboratory Press, etc.). The reactive functional group as mentioned above includes, for example, a hydroxy group, halogenated alkyl group, isothiocyanate group, avidin group, biotin group, carboxyl group, ketone group, maleimido group, active ester group, sulfonic acid halide group, carboxylic acid halide group, amino group, sulfonic acid group, pyridyldithio group, aldehyde group, and the like.

When the number of the nucleic acid chain to be bound to the substance having an affinity for the target for measurement is uneven, the number of the nucleic acid chain existing in the formed complex becomes uneven to make separation of the complex non-specific. Therefore, it is preferable to unify the number of the nucleic acid chain to be bound to the substance having an affinity for the target for measurement. In the same reason, it is appropriate for the number of the substance having an affinity for the target for measurement binding to one molecule of the nucleic acid chain to be one molecule.

In the above-mentioned binding method, when the nucleic acid chain has a functional group at both ends to which a substance having an affinity for the target for measurement can be bound, the nucleic acid chain may preliminarily be cleaved enzymatically or chemically so that the reactive functional group is introduced at one end, and then allowed to bind to the substance having an affinity for the target for measurement. Alternatively, the nucleic acid chain is allowed to bind to the substance having an affinity for the target for measurement so as to yield the intermediate to which the substance having an affinity for the target for measurement is bound at both ends, and the nucleic acid chain binding to the intermediate is cleaved enzymatically or chemically to yield the product in which the substance having an affinity for the target for measurement is bound at one end of the nucleic acid.

As the marker used in the invention, those capable of labeling a nucleic acid chain used conventionally in this field, for example, enzyme immunoassay (EIA), radioimmunoassay (RIA), fluorescence immunoassay (FIA), hybridization, and the like, may be used. Such a substance includes, for example, enzymes such as alkaline phosphatase (ALP), β-galactosidase (β-Gal), peroxidase (POD), microperoxidase, glucose oxidase (GOD), glucose-6-phosphate dehydrogenase (G6PDH), malic acid dehydrogenase, luciferase, etc.; dyes such as Coomassie Brilliant Blue R250, methyl orange, etc.; radioactive isotopes such as $^{99m}$Tc, $^{131}$I, $^{125}$I, $^{14}$C, $^{3}$H $^{32}$P, $^{35}$S, etc.; fluorescein, rhodamine, dansyl, fluorescamine, coumalin, naphthylamine, or their derivatives; rare earth fluorescent dyes [a combination of a rare earth metal, e.g., samarium (Sm), europium (Eu), terbium (Tb) or dysprosium (Dy), with a chelate compound, e.g., 4,4'-bis(1",1",1",2",2",3",3"-heptafluoro-4",6"-hexadion-6"-yl)chlorosulfo-o-terphenyl (BH-HCT), 4,7-bis(chlorosulfonyl)-1,10-phenanthroline-2,9-dicarboxylic acid (BCPDA), β-naphthyltrifluoroacetic acid (β-NTA), etc.]; fluorescent substances such as nucleic acid-binding fluorescent dye; luminescent substances such as luciferin, isoluminol, luminol, bis(2,4,6-trifluoro-phenyl)oxalate, etc.; UV absorbing substances such as phenol, naphthol, anthracene, or their derivatives; substances having a property of spin-labeling agent exemplified by compounds having an oxyl group such as 4-amino-2,2,6,6-tetramethyl-piperidin-1-oxyl, 3-amino-2,2,5,5-tetramethyl-pyrrolidin-1-oxyl, 2,6-di-t-butyl-α-(3,5-di-t-butyl-4-oxo-2,5-cyclohexadien-1-ylidene)-p-tolyloxy, etc.

The above-mentioned fluorescent dye binding to a nucleic acid emits strong fluorescence depending on binding to the nucleic acid chain. Such a nucleic acid-binding fluorescent dye includes, for example, so-called intercalator dyes which are intercalated between the bases of the nucleic acid chain [for example, acridine dyes such as acridine orange, ethidium compounds such as ethidium bromide, ethidium homodimer 1 (EthD-1), ethidium homodimer 2 (EthD-2), ethidium bromide monoazide (EMA), dihydroethidium, etc., iodide compounds such as propidium iodide, hexydium iodide, etc., 7-amino-actinomycin D (7-AAD), cyanine dimer dyes such as POPO-1, BOBO-1, YOYO-L, TOTO-1, JOJO-1, POPO-3, LOLO-1, BOBO-3, YOYO-3, TOTO-3, etc. (all are trade names of Molecular Probe); cyanine monomer dyes such as PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5, etc. (all are trade names of Molecular Probe); SYTOX dyes such as SYBR Gold, SYBR Green I and SYBR Green II, SYTOX Green, SYTOX Blue, SYTOX Orange, etc. (all are trade names of Molecular Probe)]; those binding to a minor group of DNA double helix [for example, 4',6-diamino-2-phenylindole (DAPI: trade names of Molecular Probe), pentahydrate(bis-benzimide) (Hoechst 33258: trade names of Molecular Probe), trihydrochloride (Hoechst 33342: trade names of Molecular Probe), bisbenzimide dye (Hoechst 34580: trade names of Molecular Probe), etc.]; those specifically binding to the sequence of adenine-thymine (A-T) [for example, acridine dyes such as 9-amino-6-chloro-2-methoxyacridine (ACMA), bis-(6-chloro-2-methoxy-9-acridinyl)spermine (acridine homo-dimer), etc.; for example, hydroxystilbamidine, etc.], and the like.

In the invention, a labeling method of the nucleic acid chain with a marker may be carried out in the same manner as in binding of the nucleic acid chain to the substance having an affinity for the target for measurement as mentioned above.

Use of a fluorescent dye binding to a nucleic acid as a marker may be carried out as follows.

According to a conventional manner (e.g., a method as described in Handbook of Fluorescent Probe and Research Chemicals, 7th edition, Chapter 8; Molecular Probe Inc.), marker is made contact with a nucleic acid chain (including the nucleic acid chain in a nucleic acid chain-binding affinity substance or a complex of nucleic acid chain-binding affinity substance and a target for measurement) in a solution as water or a buffer usually used in this field of hybridization or immunoassay, for example, tris-buffer, phosphate buffer, Veronal buffer, borate buffer, Good's buffer, SSC buffer, TBE buffer, TAE buffer, etc., at a suitable temperature for a suitable period of time.

In the above-mentioned method, the contact of the nucleic acid chain (including the nucleic acid chain contained in the nucleic acid chain-binding affinity substance or a complex of the nucleic acid chain-binding affinity substance and the target for measurement) with the marker may be carried out by dissolving or dispersing or suspending the nucleic acid chain, a sample containing the target for measurement, the nucleic acid chain-binding affinity substance, the marker, the complex of the nucleic acid chain-binding affinity substance and the marker, etc., directly in water or a buffer as mentioned above, or by dissolving or dispersing or suspending the respective components in water or a buffer as mentioned above to give liquid products, followed by mixing them so as to contact with each other.

In carrying out the labeling method of the nucleic acid chain with a marker in the invention, the marker may be linked directly to the nucleic acid chain or through a linker [e.g., Sulfo-SMPB, Sulfo-SMCC, EMCS, etc.] or a nucleic acid (that different from the nucleic acid chain to be labeled, attached (bound) to the substance having an affinity for the target for measurement; hereinafter abbreviated to as linker nucleic acid chain), peptide, protein, sugar, and the like (hereinafter abbreviated to as linker substance).

When the nucleic acid chain is linked to the marker through a linker substance, the binding of the nucleic acid chain to the linker substance or the binding of the linker substance to the marker may be conducted in the same manner as in binding the nucleic acid chain to the substance having an affinity for the target for measurement or in labeling the nucleic acid chain with the marker. In carrying out the label of the nucleic acid chain with the marker through a linker substance, a linker substance preliminarily labeled with the marker may be bound to the nucleic acid chain, or alternatively the linker substance may be linked to the nucleic acid chain, followed by linkage with the marker, or the nucleic acid chain, the linker substance and the marker are allowed to bind all at once.

Moreover, in the invention, the label of the nucleic acid chain with the marker may be conducted before or at the same time as or after formation of the complex of the target for measurement—(the nucleic acid chain-binding affinity substance—the marker) according to the marker to be used, as mentioned below. There is no limitation for this labeling.

Though it is difficult to generally define the concentration of the marker to be used because it depends on the kind of the marker, the concentration in a liquid mixture for making the nucleic acid chain (including the nucleic acid chain contained in the nucleic acid chain-binding affinity substance or a complex of the nucleic acid chain-binding affinity substance and the target for measurement) contact with the marker is usually 1 fM or more, preferably 1 pM or more, more preferably 1 pM to 1M, further preferably 1 nM to 1M, and particularly 1 μM to 1M.

Particularly, when a nucleic acid-binding fluorescent dye is used as a marker, the concentration in a liquid mixture for making the nucleic acid chain (including the nucleic acid chain contained in the nucleic acid chain-binding affinity substance or a complex of the nucleic acid chain-binding affinity substance and the target for measurement) contact with the marker is usually 1 fM or more, preferably 1 pM to 1M, more preferably 1 nM to 1M.

In the invention, when a sample such as sera containing a large quantity of coexisting substances (e.g., proteins, etc.) capable of binding to the nucleic acid-binding fluorescent dye other than the target for measurement is used, it is appropriate to use a marker other than the nucleic acid-binding fluorescent dye among the above-mentioned markers in order to avoid increase of the background and decrease of the signal intensity caused by association of the nucleic acid-binding fluorescent dye with the coexisting substances.

In this connection, when a somewhat purified target for measurement is used, in other words, when the sample, in addition to the target for measurement, does not contain a large quantity of coexisting substances (e.g., proteins, etc.) to which is bound the nucleic acid-binding fluorescent dye, it is preferable to use the nucleic acid-binding fluorescent dye because of the following reasons.

Since the nucleic acid-binding fluorescent dye can act to label a nucleic acid chain at a certain ratio (usually labeling at a ratio of 1 molecule for 5 to 6 bases), it is possible to increase the labeling amount (labeling efficiency) more than in use of the conventional marker. Thus sensitivity of measurement (detection) can be raised. In addition, the amount of the nucleic acid-binding fluorescent dye for labeling a nucleic acid chain can easily be adjusted by varying the length of the nucleic acid chain, and the sensitivity of measurement (detection) can be controlled optionally. For example, when the target for measurement is in a high concentration, it is possible to keep the sensitivity of measurement (detection) at low level by using a short length nucleic acid chain to reduce the amount of the nucleic acid-binding fluorescent dye for labeling a nucleic acid chain. On the other hand, when the target for measurement is in a low concentration, it is possible to raise the sensitivity of measurement (detection) by using a long length nucleic acid chain to increase the amount of the nucleic acid-binding fluorescent dye for labeling a nucleic acid chain. Thus, it becomes possible to broaden the dynamic range of measurement.

In a method for labeling a nucleic acid chain with a marker in the invention, it is preferable to bind the nucleic acid chain to the marker through a linker substance. Particularly, it is preferred to bind the nucleic acid chain to the linker substance preliminarily labeled with the marker.

When the amount of the marker used in label of the nucleic acid chain is not even, the nucleic acid chain-binding affinity substance labeled with the marker affords a broad peak in electrophoresis causing decrease of the sensitivity. In the above-mentioned method, it is possible to label the nucleic acid chain by an even amount of the marker. Particularly, when the linker substance preliminarily labeled with the marker is used, it is more preferable because the amount of the marker used in label of the linker substance can easily be adjusted in the course of preparation of the labeled linker substance.

For example, biotin is bound to a nucleic acid chain and then to avidin (or streptavidin) preliminarily labeled with a marker. Thus, the nucleic acid chain can easily be labeled under control of the amount of the marker. In another case, for example, biotin is first bound to a nucleic acid chain and then to a linker substance (for example, linker nucleic acid chain, etc.) labeled with a marker preliminarily bound to biotin through avidin (or streptavidin). Thus, the nucleic acid chain can easily be labeled under control of the amount of the marker. Moreover, since one molecule of avidin (or streptavidin) can make 4 molecules of biotin bind, it is possible to make 3 molecules of the labeled linker substance bind to raise the sensitivity of measurement (detection).

In the invention, in order to form a complex of the target for measurement—(the nucleic acid chain-binding affinity substance-marker), a sample containing the target for measurement is made mutually contact with a substance to which is bound a nucleic acid chain and which has an affinity to the target for measurement (nucleic acid chain-binding affinity substance), and a marker capable of labeling said nucleic acid chain. Finally, a complex comprising (a) the target for measurement and (b) a complex of the nucleic acid chain-binding affinity substance and the marker capable of labeling said nucleic acid chain is formed [the target for measurement—(the nucleic acid chain-binding affinity substance-marker)]. There is no limitation as far as such a complex can be produced.

Specifically, the following methods are exemplified. (1) According to the above-mentioned method, first, the nucleic acid chain contained in a substance to which is bound a nucleic acid chain and which has an affinity to the target for measurement is labeled with a marker capable of labeling said nucleic acid chain to form a complex of the nucleic acid chain-binding affinity substance and the marker (the nucleic acid chain-binding affinity substance-marker). Subsequently, this complex is mixed with a sample containing the target for measurement, for example, in water or a buffer (e.g., tris-buffer, phosphate buffer, Veronal buffer, borate buffer, Good's buffer, SSC buffer, TBE buffer, TAE buffer, etc., used in a field of hybridization, immunoassay, etc.). Thus a complex comprising the target for measurement—(the nucleic acid chain-binding affinity substance-marker) is formed. (2) A sample containing the target for measurement, a nucleic acid chain-binding affinity substance and a marker are mixed and made contact all at once in water or a buffer as mentioned above. Thus, a complex comprising the target for measurement—(the nucleic acid chain-binding affinity substance-marker) is formed. Alternatively, (3) first, a sample containing the target for measurement is made mutually contact with a nucleic acid chain-binding affinity substance in water or a buffer as mentioned above to form a complex of target for measurement-nucleic acid chain-binding affinity substance. Then, the nucleic acid chain in the resulting complex of target for measurement-nucleic acid chain-binding affinity substance is labeled with a marker to yield a complex comprising the target for measurement—(the nucleic acid chain-binding affinity substance-marker).

In the above-mentioned methods, a sample containing the target for measurement, a nucleic acid chain-binding affinity substance, a marker, a complex of nucleic acid chain-binding affinity substance-marker, etc., may be dissolved, dispersed or suspended in water or a buffer as mentioned above for mutual contact. Alternatively, they may be respectively dissolved, dispersed or suspended in water or a buffer as mentioned above to yield the respective liquid products, which are then mixed for mutual contact.

In the above-mentioned methods, when the sample containing the target for measurement is liquid, it is not necessary to dissolve, disperse or suspend it in water or a buffer as mentioned above.

In the above-mentioned method (1) for forming a complex of the target for measurement and the complex of nucleic acid chain-binding affinity substance-marker, it is difficult to generally define the concentration of the latter complex because it is variable depending on the detection limit of the target for measurement. However, it is desirous to maintain the complex at a concentration higher than that at which the complex can bind completely to the concentration of the target for measurement of the concentration corresponding to the defined detection limit in the reaction mixture. The concentration in the reaction mixture is preferably at 2-fold or more of the concentration at which the complex can bind completely to the target for measurement of the concentration corresponding to the concentration of the defined detection limit, more preferably at 5-fold or more. In the above-mentioned method (2) for formation of a complex comprising the target for measurement—(the nucleic acid chain-binding affinity substance-marker), and in the above-mentioned method (3) for formation of a complex of the target for measurement—the nucleic acid chain-binding affinity substance, it is difficult to generally define the concentration of the nucleic acid chain-binding affinity substance because it is variable depending on the detection limit of the target for measurement. However, it is desirous to maintain the nucleic acid chain-binding affinity substance at a concentration higher than that at which the substance can bind completely to the target for measurement of the concentration corresponding to the concentration of the defined detection limit in the reaction mixture. The concentration in the reaction mixture is preferably at 2-fold or more of the concentration at which the complex can bind completely to the target for measurement of the concentration corresponding to the concentration of the defined detection limit, more preferably at 5-fold or more. The concentration of the marker to be used in the methods (2) and (3) may be defined as mentioned in the method for labeling the nucleic acid chain-binding affinity substance with a marker.

In the method of the invention, it is difficult to generally define pH and the temperature for forming a complex of the target for measurement—the nucleic acid chain-binding affinity substance or a complex of the target for measurement—(the nucleic acid chain-binding affinity substance-marker), since they depend on the properties of the target for measurement or the nucleic acid chain-binding affinity substance. However, as far as they do not disturb the formation of the complexes, the formation may be conducted usually at pH 2 to 10, preferably at pH 5 to 9, and usually at a temperature of 0 to 90° C., preferably at 20 to 80° C. The reaction may be conducted for a period of a few seconds to several hours responding to the respective properties of the target for measurement and the nucleic acid chain-binding affinity substance, since the reaction time required for formation of the complex is varied depending on their properties.

A sample to which the invention is applicable may be exemplified by the followings: samples of biological origin including body fluid such as serum, plasma, cerebrospinal fluid, synovial fluid, lymph, etc., excretions such as urine, faces, etc., expectoration, purulent matter, dermal exfoliation, etc., environmental samples such as food, beverage, tap water, seawater, water of lakes and marshes, river water, factory waste water, washings for semiconductors, washings after washing of medical instruments, etc., and their processed products reconstituted by dissolving in water or a buffer usually used in this field, for example, tris-buffer, phosphate buffer, Veronal buffer, borate buffer, Good's buffer, etc.

Thus resulting complex comprising the target for measurement—(the nucleic acid chain-binding affinity substance-marker) is separated from the nucleic acid chain-binding affinity substance-marker not involved in the formation of said complex and if required from the marker. In this separation, a conventional method used in this field, so-called B/F separation procedure, can be applied, for example, an electrical separation utilizing electricity such as electrophoresis (e.g., isoelectric focusing, SDS-polyacrylamide electrophoresis, agarose gel electrophoresis, acrylamide electrophoresis), dielectrophoresis, etc., column analysis (e.g., gel filtration column analysis, ion-exchange column analysis, affinity column analysis), mass spectrometric analysis, and the like. In particular, a method used in separation of proteins or nucleic acids, for example, an electrical separation including electrophoresis such as isoelectric focusing, SDS-polyacrylamide electrophoresis, agarose gel electrophoresis, acrylamide electrophoresis, etc., or dielectrophoresis may preferably be used. More particularly, it is preferable to use capillary electrophoresis or dielectrophoresis since they can be conducted in an efficient cooling condition and under high voltage in high separation efficiency.

In the invention, the complex comprising the target for measurement—(the nucleic acid chain-binding affinity substance-marker) is generally separated from the nucleic acid chain-binding affinity substance-marker not involved in the formation of said complex and if required from the marker in the separation method as mentioned above. When a nucleic acid-binding fluorescent dye is used as a marker, the dye has such a property that it becomes a detectable state (emission of strong fluorescence) only when it labels a nucleic acid chain. As the free nucleic acid-binding fluorescent dye not involved in the formation of the complex does not influence the intended measurement and not disturb measurement of the target for measurement, when the nucleic acid-binding fluorescent dye is used as a marker, it is not necessary to separate the target for measurement—(the nucleic acid-binding affinity substance-marker) from the marker (nucleic acid-binding fluorescent dye). Similarly, when the complex comprising the target for measurement—(the nucleic acid chain-binding affinity substance-marker) is formed according to the method as mentioned above (1), that is, when, first, a complex of the nucleic acid chain-binding affinity substance and the marker is formed and then made contact with the target for measurement to form the complex comprising the target for measurement—(the nucleic acid chain-binding affinity substance-marker), after the formation of the complex of the nucleic acid chain-binding affinity substance-marker, the free marker is separated and removed beforehand, and then the complex of the nucleic acid chain-binding affinity substance-marker containing no free marker may be made contact with the target for measurement. In such a case, it is not necessary to respectively separate the target for measurement—(the nucleic acid chain-binding affinity substance-marker) and the marker. Accordingly, in such a case, it is sufficient to respectively separate the complex comprising the target for measurement—(the nucleic acid chain-binding affinity substance-marker) and the nucleic acid chain-binding affinity substance-marker not involved in the formation of the complex.

In the invention, all of the separating apparatuses, electric power sources for migration (electrophoresis), buffers, fillers, a variety of reagents such as processing solutions, etc., conventionally used in a separation process based on electrophoresis as mentioned above may be utilized. The concentration of these materials may be chosen optionally according to the per se known method. The condition for separation (e.g., pH, temperature, applied voltage, time, and so on) may properly be chosen according to the per se known method.

When the method of the invention is carried out in a μ-TAS, it is particularly preferable to carry out the separation by means of capillary chip electrophoresis or dielectrophoresis.

Capillary chip electrophoresis is a technique for conducting electrophoresis in a capillary of 100 μm or less in cross section diameter provided on a chip substrate. In this method, substances in a sample can be separated based on the difference of migration degree caused by applying some voltage inside the capillary depending on the difference of their own electric charge. The apparatus used in this method has basically the structure as shown in FIG. 1, equipped with a cross-shaped capillary structure made by a fine processing technique, and a reservoir at the capillary end for filling a buffer or sample.

The capillary chip electrophoresis is conducted for separation of substances according to the following procedures.

(1) A buffer for migration (electrophoresis) is packed in a capillary, and then a sample is applied in a sample reservoir. (2) Subsequently, some voltage is applied, for example as shown in the introduction of a sample in FIG. 1, and as a result a sample migrates from the sample reservoir in the direction of the arrow (the sideways arrow). (3) Then, the applied voltage is converted into a sample separation voltage, for example as shown in FIG. 1 (the vertical arrow), and thus only a sample existing in the capillary cross portion is introduced into a capillary for separation. The substance is separated in an optional position in the capillary for separation depending on the difference of the migration degree of the substance.

In this connection, inside the capillary, a polymer having a molecular sieve effect is packed as filler together with a buffer for migration (electrophoresis). Thus, in addition to the difference of the charge, the difference of the size of a substance contributes to the difference of the migration degree to allow more efficient separation.

There is no particular limitation for the quality of the material of capillary used in the invention as far as it has been conventionally used in this field. Specifically, such a material includes, for example, silica compounds such as glass, quartz, silicone, etc., and synthetic polymers such as polymethyl methacrylate, polymethylsiloxane, polyvinyl chloride, polyurethane, polystyrene, polysulfone, polycarbonate, polytetrafluoroethylene, etc. There is no particular limitation in the inside diameter and length as far as the target for measurement can be separated. The inside diameter is usually 1 to 1,000 μm, preferably 1 to 200 μm, more preferably 1 to 100 μm. The length is usually 0.1 mm to 100 cm, preferably 0.1 mm to 20 cm, more preferably 0.1 mm to 10 cm.

There is no particular limitation for the polymer (filler) packed in the capillary as far as it has been conventionally used in this field. Specifically, such a polymer includes, for example, polyethers such as polyethylene oxide (polyethylene glycol), polypropylene oxide, etc.; polyalkylenimines such as polyethylenimine, etc.; polyacrylic polymers such as polyacrylic acid, polyacrylate ester, methyl polyacrylate, etc.; polyamide polymers such as polyacrylamide, polymethacrylamide, etc.; polymethacrylic acid-type polymers such as polymethacrylic acid, poly-methacrylate ester, methyl polymethacrylate, etc.; polyvinyl-type polymers such as polyvinyl acetate, polyvinylpyrrolidone, polyvinyloxazolidone, etc.; water-soluble hydroxyl polymers such as pullulan, elsinan, xanthan, dextran, guar gum, etc.; water-soluble cellulose such as methylcellulose, hydroxyethylcellulose, hydroxypropylcellulose, etc.; and their derivatives, and co-polymers containing multiple kinds of monomer units constituting their polymers. The filler may be used alone or in combination of two or more members.

The molecular weight of the filler as mentioned above is usually 500 Da to 6,000 kDa, preferably 1 to 1,000 kDa, more preferably 100 to 1,000 kDa.

The concentration of the filler used as mentioned above is chosen optionally within the range usually employed in this field, that is, usually 0.01 to 40% (w/v), preferably 0.01 to 20% (w/v), more preferably 0.1 to 10% (w/v).

When the above-mentioned filler is added to a buffer for migration (electrophoresis), the viscosity of the buffer is usually 2 to 1,000 centi-poise, preferably 5 to 200 centi-poise, more preferably 10 to 100 centi-poise.

There is no particular limitation for the buffer for migration as far as it has usually been used in this field. Specifically, such a buffer includes those used in a field of hybridization, immunoassay, etc., for example, tris-buffer, phosphate buffer, Veronal buffer, borate buffer, Good's buffer, SSC buffer, TBE buffer, TAE buffer, etc. These buffers may be usually used in a concentration of 0.1 mM to 10M, preferably 1 mM to 5M, more preferably 5 mM to 1M. The pH of the buffer may be in any range where the substance separation is not adversely affect and is usually 2 to 13, preferably 4 to 11, more preferably 5 to 9.

The applied voltage may be chosen from the range usually employed in this field, usually 5 to 2,000 V/cm$^2$, preferably 10 to 1,000 V/cm$^2$, more preferably 50 to 500V/cm$^2$.

The mode for carrying out the invention is described in the followings.

[Separation Method 1]

Figure 2:
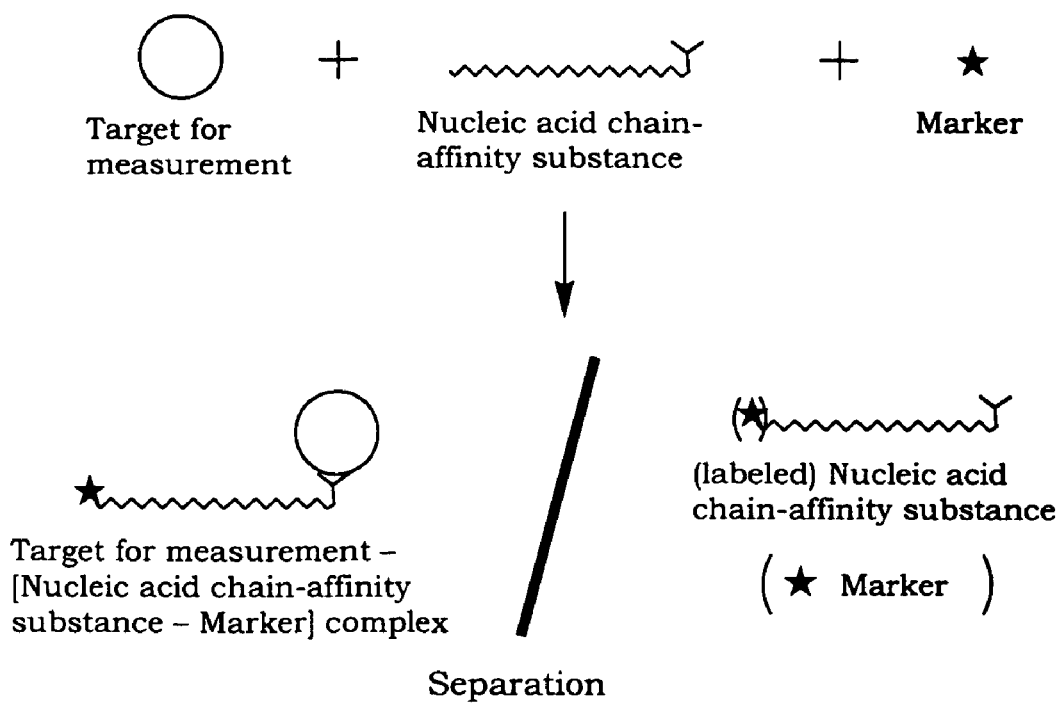
FIG. 2 shows schematically the separation method 1 of the invention, that is, the principle in a case using 1 species of nucleic acid chain-binding affinity substance for a target for measurement.

An example of using one species of the nucleic acid chain-binding affinity substance for a target for measurement in the invention is shown schematically in FIG. 2.

First, a sample containing a target for measurement, one species of a substance to which is bound a nucleic acid chain and which has an affinity to the target for measurement (nucleic acid chain-binding affinity substance), and a marker capable of labeling said nucleic acid chain are formed into a complex of the target for measurement—[the nucleic acid chain-binding affinity substance-marker], followed by electrophoretic separation from the nucleic acid chain-binding affinity substance-marker not involved in the formation of said complex and if required from the marker.

The target for measurement separable in the above-mentioned method includes those of which the pI has usually the difference of 0.1 or more, preferably 0.5 or more, more preferably 1.0 or more, from the pH value of the buffer used in electrophoretic separation.

There is no particular limitation for the size (molecular weight) of the target for measurement, but it is usually 100 Da or more, preferably 300 Da to 2,000 kDa, more preferably 500 Da to 1,000 kDa.

Relative to the above-mentioned method, the following items are as described above: a nucleic acid chain; a substance having an affinity for the target for measurement; a marker; a sample containing the target for measurement; a method for binding a nucleic acid chain to a substance having an affinity for the target for measurement; a method for labeling a nucleic acid chain with a marker; and a method for forming a sample containing a target for measurement, a substance to which is bound a nucleic acid chain and which has an affinity to the target for measurement (nucleic acid chain-binding affinity substance), and a marker capable of labeling said nucleic acid chain into a complex of the target for measurement—(the nucleic acid chain-binding affinity substance-marker).

Relative to the above-mentioned method, as a method for separating the resulting complex of the target for measurement—(the nucleic acid chain-binding affinity substance-marker) from the nucleic acid chain-binding affinity substance-marker not involved in the formation of the complex and if required from the marker, any type of so-called B/F separation methods usually used in this field may be applied as mentioned above. Particularly, an electrophoretic method used in separation of proteins or nucleic acids is generally used, and capillary (chip) electrophoresis or dielectrophoresis is preferred. The separating apparatuses, electric power sources for migration, buffers, fillers, a variety of reagents such as processing solutions, their concentration in using, the quality of a material for the capillary, conditions for separation (e.g., pH, temperature, applied voltage, time, and so on) are the same as mentioned above.

[Separation Method 2]

Figure 3:
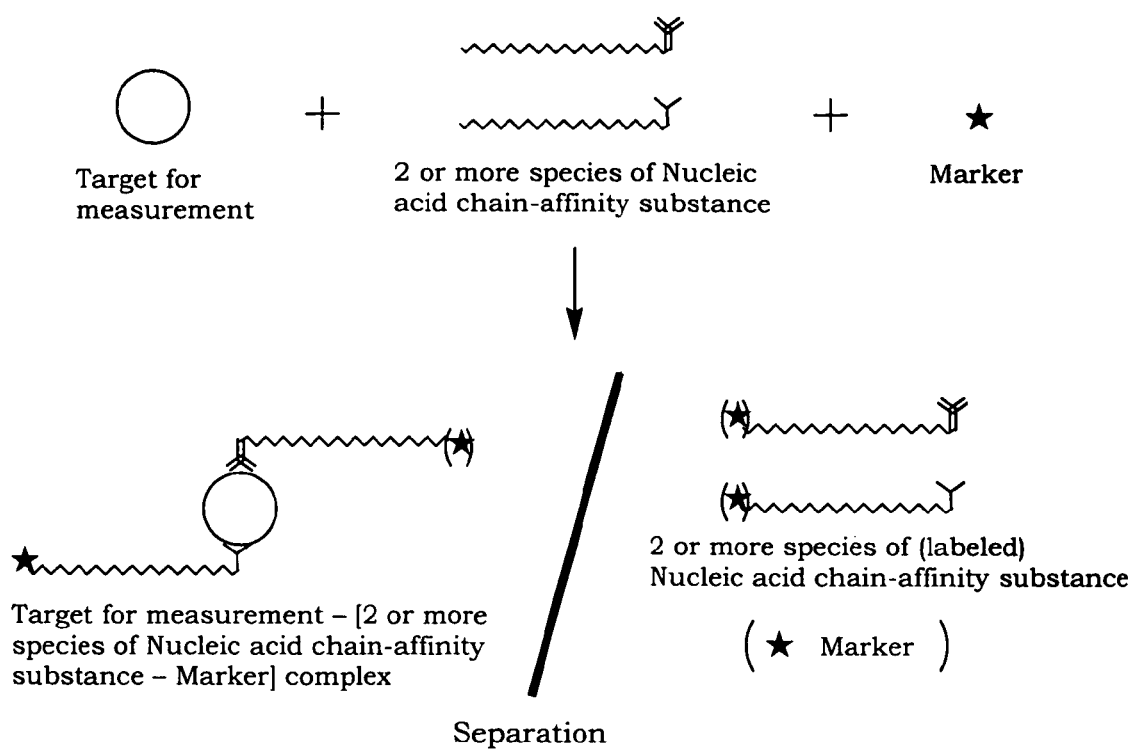
FIG. 3 shows schematically the separation method 2 of the invention, that is, the principle in a case using 2 or more species of nucleic acid chain-binding affinity substances for a target for measurement.

In the method of the invention, one species of a nucleic acid chain-binding affinity substance is used in combination with one or more species of other nucleic acid chain-binding affinity substances. That is, the use of 2 or more species of the nucleic acid chain-binding affinity substances improves separation ability for the target for measurement. An example of using 2 or more species of the nucleic acid chain-binding affinity substances for a target for measurement is shown schematically in FIG. 3.

First, a sample containing a target for measurement, 2 or more species of substances to which is bound a nucleic acid chain and which have an affinity for the target for measurement and respectively different binding sites for the target for measurement, and a marker capable of labeling said nucleic acid chain are formed into a complex of the target for measurement—[2 or more species of the nucleic acid chain-binding affinity substances-marker], followed by electrophoretic separation of the complex from 2 or more species of the nucleic acid chain-binding affinity substance-markers not involved in the formation of said complex and if required from the marker.

Among the above-mentioned targets for measurement, the target separated in the above-described method has mutually different 2 or more binding sites to which can bind different 2 or more species of the nucleic acid chain-binding affinity substances.

The nucleic acid chains in bound to 2 or more species of the nucleic acid chain-binding affinity substances which are used in the above-described method are as mentioned above. The length of the respective nucleic acid chains may be the same or different, allowing the separation of the complex of the target for measurement—[2 or more species of the nucleic acid chain-binding affinity substances-marker] from 2 or more species of the nucleic acid chain-binding affinity substance-markers not involved in the formation of said complex and if required from the marker. More specifically, the relation between the nucleic acid chain in the formed complex and that of 2 or more species of the nucleic acid chain-binding affinity substances is represented by (the sum total of the nucleic acid chain length in the complex—the nucleic acid chain length of the longest nucleic acid chain-binding affinity substance among 2 or more species of the nucleic acid chain-binding affinity substances)/(the sum total of the nucleic acid chain length in the complex)=X, and the value X is usually in the range of $0 < X < 1$, preferably $0.001 \leq X < 1$, more preferably $0.01 \leq X < 1$, further preferably $0.1 \leq X < 1$, and particularly $0.5 \leq X < 1$.

As 2 or more species of substances to which is bound a nucleic acid chain and which have an affinity for the target for measurement and respectively different binding sites for the target for measurement, 2 or more species of substances having respectively different binding sites for the target for measurement may be chosen from the substances to which is bound a nucleic acid chain and which have an affinity for the target for measurement.

In the above-mentioned method, it is general to label all of the nucleic acid chain-binding affinity substances with a marker, but sufficient to label at least one species of the nucleic acid chain-binding affinity substances with a marker.

The other species of the nucleic acid chain-binding affinity substances may be labeled or not with a marker.

In such a case, the finally formed complex of the target for measurement—(2 or more species of the nucleic acid chain-binding affinity substances-marker) may be represented by (the nucleic acid chain-binding affinity substance)l—the target for measurement—(the nucleic acid chain-binding affinity substance-marker)m [wherein l indicates an integer of 0 or more, m indicates an integer of 1 or more, and l+m is 2 or more].

In this connection, in the above-mentioned method, 1 or 2 or more species of the markers may be used.

Relative to the above-mentioned method, the following items are the same as described above: a marker; a sample containing the target for measurement; a method for binding a nucleic acid chain to a substance having an affinity for the target for measurement; a method for labeling a nucleic acid chain with a marker; and a method for forming a sample containing a target for measurement, 2 or more species of a substances to which is bound a nucleic acid chain and which have an affinity for the target for measurement and respectively different binding sites for the target for measurement (2 or more species of the nucleic acid chain-binding affinity substances), and a marker capable of labeling said nucleic acid chain into a complex of the target for measurement—(2 or more species of the nucleic acid chain-binding affinity substance-markers).

Relative to the above-mentioned method, as a method for separating the resulting complex of the target for measurement—(2 or more species of the nucleic acid chain-binding affinity substance-markers) from 2 or more species of the nucleic acid chain-binding affinity substance-markers not involved in the formation of the complex and if required from the marker, any type of so-called B/F separation methods usually used in this field may be applied as mentioned above. Particularly, an electrophoretic method used in separation of proteins or nucleic acids is generally used, and capillary (chip) electrophoresis or dielectrophoresis is preferred. The separating apparatuses, electric power sources for migration, buffers, fillers, a variety of reagents, their concentration in using, the quality of a material for the capillary, conditions for separation (e.g., pH, temperature, applied voltage, time, and so on) are the same as mentioned above.

In the method of the invention, a substance to which is bound a nucleic acid chain and which has an affinity for the target for measurement and a marker capable of labeling said nucleic acid chain can be bound respectively to 2 or more species of the targets for measurement so as to have nucleic acid chains having a different length from each other and yield 2 or more species of complexes of the target for measurement-nucleic acid chain-binding affinity substance-marker. Thus, it becomes possible to separate 2 or more species of the complexes respectively from the nucleic acid chain-binding affinity substance-marker not involved in the formation of the complexes and if required from the marker. In other words, multiple targets for measurement can be separated at the same time.

The above-mentioned method can be classified roughly into 2 types depending on the properties of the used substance having an affinity for the target for measurement, that is, a method in which at least one species of substances having an affinity for all of 2 or more types of the targets for measurement is used, and a method in which 2 or more species of substances having an affinity for only one type of 2 or more types of targets for measurement are used.

[Separation Method 3]

Figure 4:
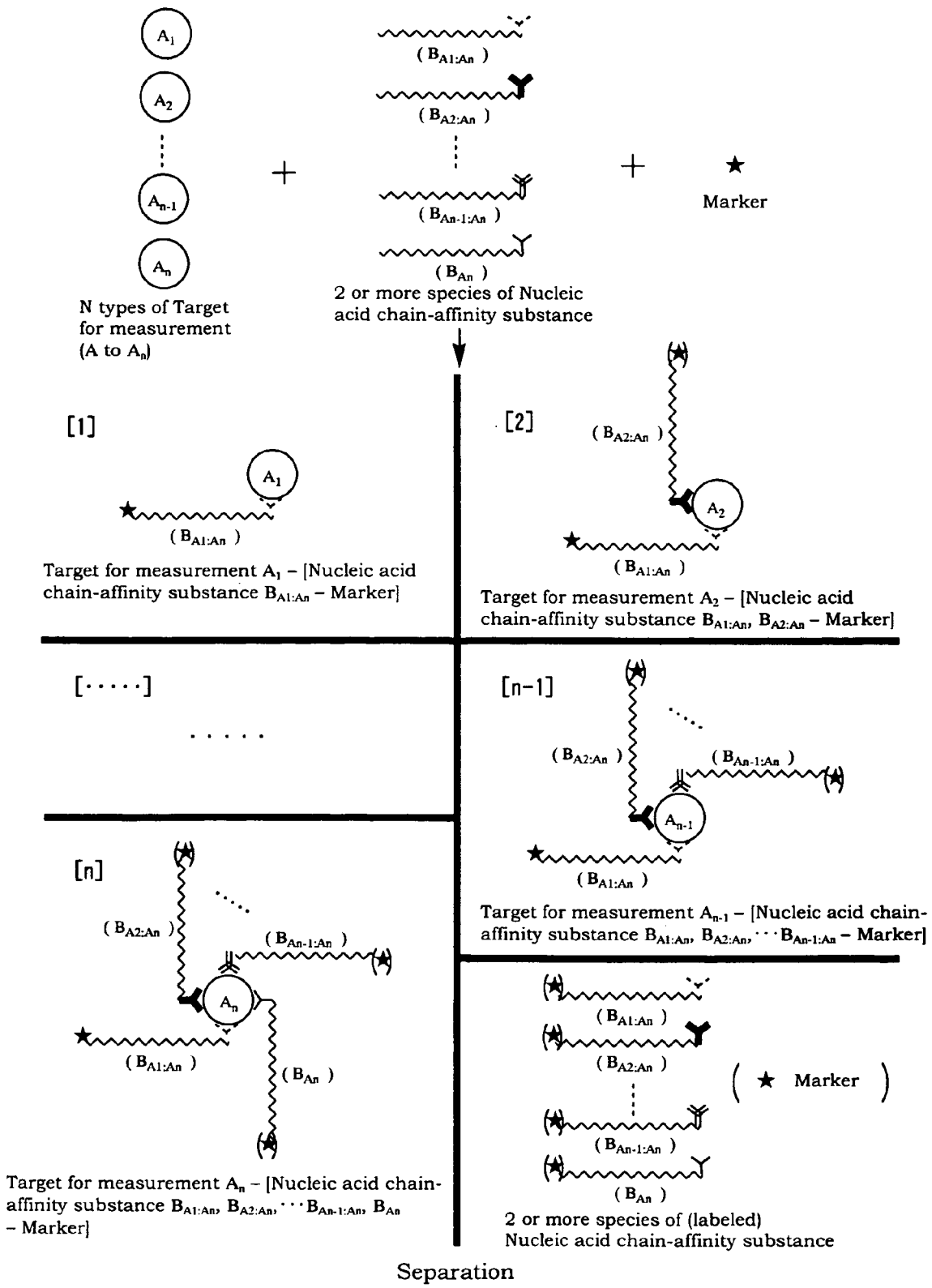
FIG. 4 shows schematically the separation method 3 of the invention, that is, the principle in a case using at least 1 species of substance having an affinity for all of 2 or more types of targets for measurement.

First, a method in which at least one species of substances having an affinity for all of 2 or more types of the targets for measurement is used is shown schematically in FIG. 4.

The method comprises first forming (a) a sample containing mutually different n types (wherein n is an integer of 2 or more) of targets $A_1$, $A_2$, $A_3$, $A_{n-1}$ and $A_n$ for measurement, (b)(1) a substance to which is bound a nucleic acid chain and which has an affinity to all of n types of the targets for measurement $A_1$ to $A_n$ (nucleic acid chain-binding affinity substance $B_{A1:An}$), (2) a substance to which is bound a nucleic acid chain and which has an affinity to all of the targets for measurement $A_2$ to $A_n$ except for $A_1$ (nucleic acid chain-binding affinity substance $B_{A2:An}$), (3) a substance to which is bound a nucleic acid chain and which has an affinity to all of the targets for measurement $A_3$ to $A_n$ except for $A_1$ and $A_2$ (nucleic acid chain-binding affinity substance $B_{A3:An}$), ..., (n−1) a substance to which is bound a nucleic acid chain and which has an affinity to the targets $A_{n-1}$ and $A_n$ except for all of $A_1$ to $A_{n-2}$ (nucleic acid chain-binding affinity substance $B_{An-1:An}$), and (n) a substance to which is bound a nucleic acid chain and which has an affinity only to the target $A_n$ except for all of $A_1$ to $A_{n-1}$ (nucleic acid chain-binding affinity substance $B_{An}$), and (c) a marker capable of labeling said nucleic acid chain, into [1] a complex of the target $A_1$ for measurement—nucleic acid chain-binding affinity substance $B_{A1:An}$—marker, [2] a complex of the target $A_2$ for measurement—nucleic acid chain-binding affinity substance $B_{A1:An}$ and nucleic acid chain-binding affinity substance $B_{A2:An}$—marker, [3] a complex of the target $A_3$ for measurement—nucleic acid chain-binding affinity substance $B_{A1:An}$, nucleic acid chain-binding affinity substance $B_{A2:An}$ and nucleic acid chain-binding affinity substance $B_{A3:An}$—marker, ..., [n−1] a complex of the target $A_{n-1}$ for measurement—nucleic acid chain-binding affinity substance $B_{A1:An}$, nucleic acid chain-binding affinity substance $B_{A2:An}$, nucleic acid chain-binding affinity substance $B_{A3:An}$, ... and nucleic acid chain-binding affinity substance $B_{An-1:An}$—marker, and [n] a complex of the target $A_n$ nucleic acid chain-binding affinity substance $B_{A1:An}$, nucleic acid chain-binding affinity substance $B_{A2:An}$, nucleic acid chain-binding affinity substance $B_{A3:An}$, ... nucleic acid chain-binding affinity substance $B_{An-1:An}$ and nucleic acid chain-binding affinity substance $B_{An}$—marker, and then mutually separating the respective complexes [1] to [n] from complexes of the respective nucleic acid chain-binding affinity substances (1) to (n) and the markers not involved in the formation of said complexes and if required from the markers.

The n types of the targets for measurement separated in the above-mentioned method mean that among the above-mentioned targets for measurement all of the targets 1 to n for measurement have at least one binding site which is common with all of the targets 1 to n for measurement and to which a nucleic acid chain-binding affinity substance is capable of binding. In addition, among them, the followings are also meant: the targets 2 to n for measurement have a binding site which is common with the targets 2 to n for measurement other than the target 1 for measurement and to which a nucleic acid chain-binding affinity substance is capable of binding (the binding site not contained in the target 1 or that contained in the target 1 but inhibited by some factor the binding of the nucleic acid chain-binding affinity substance); ... the targets n−1 to n for measurement have a binding site which is common with the targets n−1 to n for measurement other than the target 1 to n−2 for measurement and to which a nucleic acid chain-binding affinity substance is capable of binding (the binding site not contained in the targets 1 to n−2 for measurement or that contained in the targets 1 to n−2 for measurement but inhibited by some factor the binding of the nucleic acid chain-binding affinity substance); and the target n for measurement have a binding site which is contained only in the target n for measurement and to which a nucleic acid chain-binding affinity substance is capable of binding (the binding site not contained in any of the targets 1 to n−1 for measurement or that contained in the targets 1 to n−1 for measurement but inhibited by some factor the binding of the nucleic acid chain-binding affinity substance). In the above-mentioned method, the phrase "contained but inhibited by some factor the binding of the nucleic acid chain-binding affinity substance" means, for example, that the structure of the binding site is not changed but the binding of the nucleic acid chain-binding affinity substance to the binding site on the target for measurement is inhibited by the neighboring structure (e.g., sugar chain, etc.), or that a certain substance (e.g., lectin, etc.) attaching (binding) to the neighbor of the binding site is inhibiting the binding of the nucleic acid chain-binding affinity substance to the binding site on the target for measurement.

In the above-mentioned method, when only one species of the substance to which is bound a nucleic acid chain and which has an affinity for all of the n types of targets $A_1$ to $A_n$ for measurement (nucleic acid chain-binding affinity substance $B_{A1:An}$) is used, in other words, when among a variety of the separated complexes there is a complex to which only one species of the nucleic acid chain-binding substances binds, it is preferable for the above-mentioned targets for measurement that the pI in at least one of the targets for measurement contained in the complex has the difference of 0.1 or more, preferably 0.5 or more, more preferably 1.0 or more, from the pH of the buffer used in electrophoretic separation.

The above-mentioned method is useful in measuring a molecule containing 2 or more species of substances having the same action or a molecule containing 2 or more species of substances having a similar structure but mutually different actions such as isozymes, isoforms, hormones, etc., and has the properties as mentioned above. Such a molecule is selected from, for example, enzymes such as amylase (e.g., pancreatic type, salivary gland type, X type, etc.), alkaline phosphatase (e.g., hepatic, osteoid, placental, small intestinal, etc.), acidic phosphatase (e.g., PAP, etc.), γ-glutamyl transferase (e.g., renal, pancreatic, hepatic, etc.), lipase (e.g., pancreatic, gastric, etc.), creatine kinase (e.g., CK-1, CK-2, mCK, etc.), lactic acid dehydrogenase (e.g., LDH1 to LDH5, etc.), glutamic acid-oxaloacetic acid transaminase (e.g., ASTm, ASTs, etc.), glutamic acid-pyruvic acid transaminase (e.g., ALTm, ALTs, etc.), cholineesterase (e.g., ChE1 to ChE5, etc.), leucine aminopeptidase (e.g., C-LAP, AA, CAP, etc.), renin, protein kinase, tyrosine kinase, and the like; physiologically active substances such as steroid hormones, human chorionic gonadotropin (hCG family), prolactin, thyroid-stimulating hormone (TSH family), luteinizing hormone (LH family), and the like; cancer-relating antigens such as prostate specific antigen (PSA family), $\alpha^2$-macroglobulin, carcinoembryonic antigen (e.g., CEA, NCA, NCA-2, NFA, etc.), α-fetoprotein (e.g., L1 to L3, etc.), and the like.

The number n of the n types of the targets for measurement in the above-mentioned method is usually 2 or more, preferably 2 to 10, more preferably 2 to 5.

The nucleic acid chain in a variety of the nucleic acid chain-binding affinity substances which is used in the above-mentioned method is as mentioned above. The respective nucleic acid chains may be the same or different each other in their length, which may properly be chosen so that the complexes [1] to [n] respectively can be separated from the complexes (1) to (n) of the nucleic acid chain-binding affinity substances and the marker not involved in the formation of the former complexes, and if required from the marker. More specifically, for example, when n types of the targets for measurement are intended to separate with p species (wherein p is an integer equal to or larger than n) of the nucleic acid chain-binding affinity substances, the relation between the nucleic acid chain in n types of the respective complexes and that in p types of the respective nucleic acid chain-binding affinity substances can be represented by the following formulae. (1) (Among n species of the complexes and p species of the nucleic acid chain-binding affinity substances, the sum total of the nucleic acid chain length in the complex or the nucleic acid chain-binding affinity substance of which the total sum of the attached (bound) nucleic acid chain length is largest—the sum total of the nucleic acid chain length in the complex or the nucleic acid chain-binding affinity substance of which the total sum of the attached (bound) nucleic acid chain length is 2nd rank)/the sum total of the nucleic acid chain length in the complex or the nucleic acid chain-binding affinity substance of which the total sum of the attached (bound) nucleic acid chain length is largest; (2) (the sum total of the nucleic acid chain length in the complex or the nucleic acid chain-binding affinity substance of which the total sum of the attached (bound) nucleic acid chain length is 2nd rank—the sum total of the nucleic acid chain length in the complex or the nucleic acid chain-binding affinity substance of which the total sum of the attached (bound) nucleic acid chain length is 3rd rank)/the sum total of the nucleic acid chain length in the complex or the nucleic acid chain-binding affinity substance of which the total sum of the attached (bound) nucleic acid chain length is 2nd rank; . . . ; and (n+p−1) [the sum total of the nucleic acid chain length in the complex or the nucleic acid chain-binding affinity substance of which the total sum of the attached (bound) nucleic acid chain length is n+p−1 rank—the sum total of the nucleic acid chain length in the complex or the nucleic acid chain-binding affinity substance of which the total sum of the attached (bound) nucleic acid chain length is n+p rank (smallest)]/the sum total of the nucleic acid chain length in the complex or the nucleic acid chain-binding affinity substance of which the total sum of the attached (bound) nucleic acid chain length is n+p−1 rank. In these formulae, the resulting value (X) is usually in the range of 0<X<1, preferably $0.001 \leq X < 1$, more preferably $0.01 \leq X < 1$, further preferably $0.1 \leq X < 1$, and particularly $0.5 \leq X < 1$.

In the above-mentioned method, it is not necessary to consider the condition as mentioned above for separation of the respective free nucleic acid chain-binding affinity substances because the separation is unnecessary.

As the substance to which is bound a nucleic acid chain and which has an affinity for the target for measurement, at least n members of the substances may be chosen properly from the above-mentioned substances to which is bound a nucleic acid chain and which have an affinity for the target, as follows: (1) among n types of the targets for measurement, a substance having an affinity for all of the targets 1 to n for measurement (nucleic acid chain-binding affinity substance $B_{A1:An}$), (2) a substance having an affinity to the targets 2 to n for measurement except for the target 1 for measurement (nucleic acid chain-binding affinity substance $B_{A2:An}$) . . . , (n−1) a substance having an affinity to the targets n−1 to n for measurement except for the targets 1 to n−2 for measurement (nucleic acid chain-binding affinity substance $B_{An-1:An}$), and (n) a substance having an affinity to the target n for measurement except for the targets for measurement 1 to n−1 (nucleic acid chain-binding affinity substance $B_{An}$).

The nucleic acid chain-binding affinity substance $B_{A1:An}$, nucleic acid chain-binding affinity substance $B_{A2:An}$, nucleic acid chain-binding affinity substance $B_{A3:An}$, . . . , nucleic acid chain-binding affinity substance $B_{An-1:An}$, and nucleic acid chain-binding affinity substance $B_{An}$, used in the above-mentioned method may be used alone or in combination of 2 or more species.

In the above-mentioned method, at least one species of the nucleic acid chain-binding affinity substances contained in the complex [1] to [n] can be labeled with a marker in order to conduct the intended measurement. Though other nucleic acid chain-binding affinity substances may be labeled or not labeled, it is preferable to label the nucleic acid chain-binding affinity substances (nucleic acid chain-binding affinity substance $B_{A1:An}$) for all n types of the targets for measurement with a marker, and it is general to label all of the nucleic acid chain-binding affinity substances with a marker.

The marker used in the above-mentioned method may be used alone or in combination of 2 or more species. For example, the species of the marker to be used may be varied according to the properties of the specific nucleic acid chain-binding affinity substances. Thus the marker in 2 or more species of the complexes of the specific target for measurement-specific nucleic acid chain-binding affinity substance—the marker can be varied. Accordingly, it becomes possible to easily distinguish the formed complex, i.e., the species of the target for measurement.

Relative to the above-mentioned method, the following items are the same as described above: a marker; a sample containing the target for measurement; a method for binding a nucleic acid chain to a substance having an affinity for the target for measurement; a method for labeling a nucleic acid chain with a marker; and a method for forming the complex.

In the above-mentioned method, the resulting n types of the complexes [1] to [n]{[1] complex of target $A_1$ for measurement-nucleic acid chain-binding affinity substance $B_{A1:An}$—marker; [2] complex of target $A_2$ for measurement-nucleic acid chain-binding affinity substance $B_{A1:An}$ and nucleic acid chain-binding affinity substance $B_{A2:An}$—marker; [3] complex of target $A_3$ for measurement-nucleic acid chain-binding affinity substance $B_{A1:An}$, nucleic acid chain-binding affinity substance $B_{A2:An}$ and nucleic acid chain-binding affinity substance $B_{A3:An}$—marker; . . . ; [n−1] complex of target $A_{n-1}$ for measurement-nucleic acid chain-binding affinity substance $B_{A1:An}$, nucleic acid chain-binding affinity substance $B_{A2:An}$, nucleic acid chain-binding affinity substance $B_{A3:An}$, and nucleic acid chain-binding affinity substance $B_{An-1:An}$—marker; and [n] complex of target for measurement $A_n$—nucleic acid chain-binding affinity substance $B_{A1:An}$, nucleic acid chain-binding affinity substance $B_{A2:An}$, nucleic acid chain-binding affinity substance $B_{A3:An}$, . . . ; nucleic acid chain-binding affinity substance $B_{An-1:An}$—and nucleic acid chain-binding affinity substance $B_{An}$-marker} are separated from 2 or more species of the nucleic acid chain-binding affinity substance-markers, and if required from the marker. In this separation, a conventional method used in this field, so-called B/F separation procedure, can be applied in the same manner as mentioned above. Particularly, an electrophoretic method used in separation of proteins or nucleic acids is generally used, and capillary (chip) electrophoresis is preferred. The separating apparatuses, electric power sources for migration, buffers, fillers, a variety of reagents such as processing solutions, their concentration in using, the quality of a material for the capillary, conditions for separation (e.g., pH, temperature, applied voltage, time, and so on) are the same as mentioned above.

[Separation Method 4]

The followings will explain a method for using 2 or more species of substances which have an affinity for only one of 2 or more types of the targets for measurement.

In this method, a sample containing 2 or more types of targets for measurement, 2 or more species of substances which have an affinity for only one of 2 or more types of the targets for measurement and to which is bound a nucleic acid (hereinafter sometimes abbreviated to as a specific nucleic acid chain-binding affinity substance), and a marker capable of labeling the nucleic acid chain are formed into 2 or more species of complexes of the specific targets for measurement—the specific nucleic acid chain-binding affinity substance-marker, which are then respectively separated from the specific nucleic acid chain-binding affinity substance-marker not involved in the formation of the complexes and if required from the marker by electrophoresis.

The above-mentioned method for separation is based on the difference of electrophoretic migration in 2 or more species of complexes of the specific targets for measurement—the specific nucleic acid chain-binding affinity substance-marker. The methods for differentiating the electrophoretic migration between 2 or more species of the complexes may be classified roughly into 2 categories, that is, (1) a method for giving a difference in the number of the specific nucleic acid chain-binding affinity substances to be bound to 2 or more types of the targets for measurement, and (2) a method for giving a difference in the size (chain length) of the nucleic acid chain contained in the specific nucleic acid chain-binding affinity substances to be bound to 2 or more species of the targets for measurement.

In the above-mentioned method, the markers, the sample containing targets for measurement, the method for binding a nucleic acid chain to a substance having an affinity for the target for measurement, the method for labeling the nucleic acid chain with a marker, and the method for forming the complex are the same as mentioned above.

[Separation Method 4-a]

Figure 5:
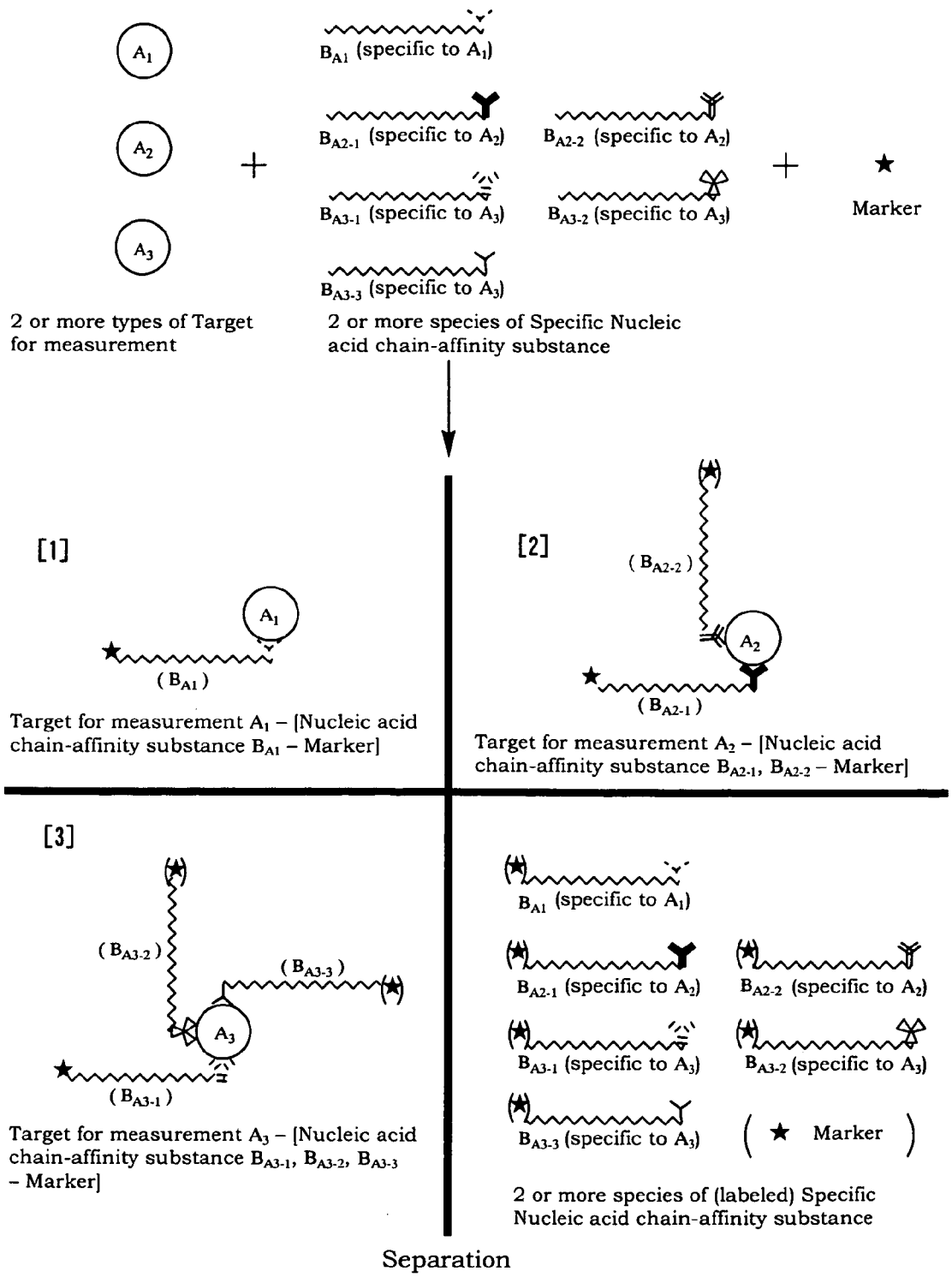
FIG. 5 shows schematically the separation method 4-a of the invention, that is, the principle how to vary the number of specific nucleic acid chain-binding affinity substances to be bound to 2 or more types of targets for measurement respectively.

First, a method for giving a difference in the number of the specific nucleic acid chain-binding affinity substances to be bound to 2 or more types of the targets for measurement is shown schematically in FIG. 5.

First, a sample containing 2 or more types of targets for measurement of which the number of the sites binding to substances having an affinity only for the respective targets for measurement is different, 2 or more species of substances to which is bound a nucleic acid chain and which have an affinity for only one of the intended targets (specific nucleic acid chain-binding affinity substances), and a marker capable of labeling the nucleic acid chain are formed into 2 or more species of complexes of the specific targets—the specific nucleic acid chain-binding affinity substances-marker, which are then respectively separated from the specific nucleic acid chain-binding affinity substances-marker not involved in the formation of the complexes and if required from the marker by electrophoresis.

As 2 or more types of the targets for measurement separated in the above-mentioned method, among the targets for measurement as mentioned above and molecules containing 2 or more species of substances having the same action or molecules containing 2 or more species of substances having a similar structure but mutually different actions as isozymes, isoforms, hormones, etc., those for which there is a substance having an affinity only for the respective targets for measurement and in which the number of the nucleic acid chain-binding affinity substances to be bound to 2 or more of the respective targets for measurement is different are included. When there is a complex to which is bound only one species of the specific nucleic acid chain-binding affinity substance in a variety of the separated complexes, it is desirous for the above-mentioned targets for measurement that the pI in at least the target for measurement contained in the complex has the difference of 0.1 or more, preferably 0.5 or more, more preferably 1.0 or more, from the pH of the buffer used in electrophoretic separation.

In the above-mentioned method, the number of 2 or more types of the targets for measurement may be usually 2 or more, preferably 2 to 10, and more preferably 2 to 5, though there is no particular limitation.

Two or more species of the nucleic acid chains in the specific nucleic acid chain-binding affinity substance which are used in the above-mentioned method are as mentioned above. The respective nucleic acid chains may be the same or different each other in their length, which may properly be chosen so that 2 or more species of the complexes of the specific targets for measurement—the specific nucleic acid chain-binding affinity substances-marker can be separated from the specific nucleic acid chain-binding affinity substance-marker not involved in the formation of the complexes, and if required from the marker. In this operation, the nucleic acid chain of the same chain length is generally used. More specifically, for example, when n types of targets for measurement are separated with p species (p has the same meanings as mentioned above) of the specific nucleic acid chain-binding affinity substances, the relation between the nucleic acid chain contained in n species of the formed complexes and that contained in p species of the respective specific nucleic acid chain-binding affinity substances used may be represented by the followings. (1) (Among n species of the complexes and p species of the specific nucleic acid chain-binding affinity substances, the sum total of the nucleic acid chain length in the complex or the specific nucleic acid chain-binding affinity substance of which the total sum of the attached (bound) nucleic acid chain length is largest—the sum total of the nucleic acid chain length in the complex or the specific nucleic acid chain-binding affinity substance of which the total sum of the attached (bound) nucleic acid chain length is 2nd rank)/the sum total of the nucleic acid chain length in the complex or the specific nucleic acid chain-binding affinity substance of which the total sum of the attached (bound) nucleic acid chain length is largest; (2) (the sum total of the nucleic acid chain length in the complex or the specific nucleic acid chain-binding affinity substance of which the total sum of the attached (bound) nucleic acid chain length is 2nd rank—the sum total of the nucleic acid chain length in the complex or the specific nucleic acid chain-binding affinity substance of which the total sum of the attached (bound) nucleic acid chain length is 3rd rank)/the sum total of the nucleic acid chain length in the complex or the specific nucleic acid chain-binding affinity substance of which the total sum of the attached (bound) nucleic acid chain length is 2nd rank; . . . ; and (n+p−1) [the sum total of the nucleic acid chain length in the complex or the specific nucleic acid chain-binding affinity substance of which the total sum of the attached (bound) nucleic acid chain length is n+p−1 rank—the sum total of the nucleic acid chain length in the complex or the specific nucleic acid chain-binding affinity substance of which the total sum of the attached (bound) nucleic acid chain length is n+p rank (smallest)]/the sum total of the nucleic acid chain length in the complex or the specific nucleic acid chain-binding affinity substance of which the total sum of the attached (bound) nucleic acid chain length is n+p−1 rank. In these formulae, the resulting value (X) is usually in the range of 0<X<1, preferably 0.001≦X<1, more preferably 0.01≦X<1, further preferably 0.1≦X<1, and particularly 0.5≦X<1.

In the above-mentioned method, it is not necessary to consider the condition as mentioned above for separation of the respective free specific nucleic acid chain-binding affinity substances because the separation is unnecessary.

As the substances to which is bound a nucleic acid chain and which have an affinity for the specific target for measurement, those having an affinity only for the intended specific target separated may properly be chosen from the substances to which is bound a nucleic acid chain and which have an affinity for the target for measurement as mentioned above.

In the above-mentioned method, the number of the specific nucleic acid chain-binding affinity substances to be bound to the specific target for measurement is not necessary to be only one at the lowest and 2 or more species may be used.

When 2 or more species of the specific nucleic acid chain-binding affinity substances are used, it is general to label all of them with a marker, but it is sufficient to label at least one species of the specific nucleic acid chain-binding affinity substances with a marker. The other species of the specific nucleic acid chain-binding affinity substances may be labeled or not with a marker.

In the above-mentioned method, the marker may be used alone or in combination of 2 or more species. For example, the kinds of the marker may be varied according to the properties of the specific nucleic acid chain-binding affinity substance. In such a case, since the kinds of the markers are mutually different between the complexes of the specific targets for measurement—the specific nucleic acid chain-binding affinity substances-markers, it is possible to easily distinguish the formed complexes, i.e., the kinds of the targets for measurement.

In the above-mentioned method, the markers, the sample containing targets for measurement, the method for binding a nucleic acid chain to a substance having an affinity for the target for measurement, the method for labeling the nucleic acid chain with a marker, and the method for forming the complex are the same as mentioned above.

In the above-mentioned method, thus resulting 2 or more species of the complexes of the specific targets for measurement—the specific nucleic acid chain-binding affinity substances-marker are respectively separated from 2 or more species of the specific nucleic acid chain-binding affinity substance-markers, and if required from the marker. In this separation, a conventional method used in this field, so-called B/F separation procedure, can be applied in the same manner as mentioned above. Particularly, an electrophoretic method used in separation of proteins or nucleic acids is generally used, and capillary (chip) electrophoresis is preferred. The separating apparatuses, electric power sources for migration, buffers, fillers, a variety of reagents such as processing solutions, their concentration in using, the quality of a material for the capillary, conditions for separation (e.g., pH, temperature, applied voltage, time, and so on) are the same as mentioned above.

[Separation Method 4-b]

Figure 6:
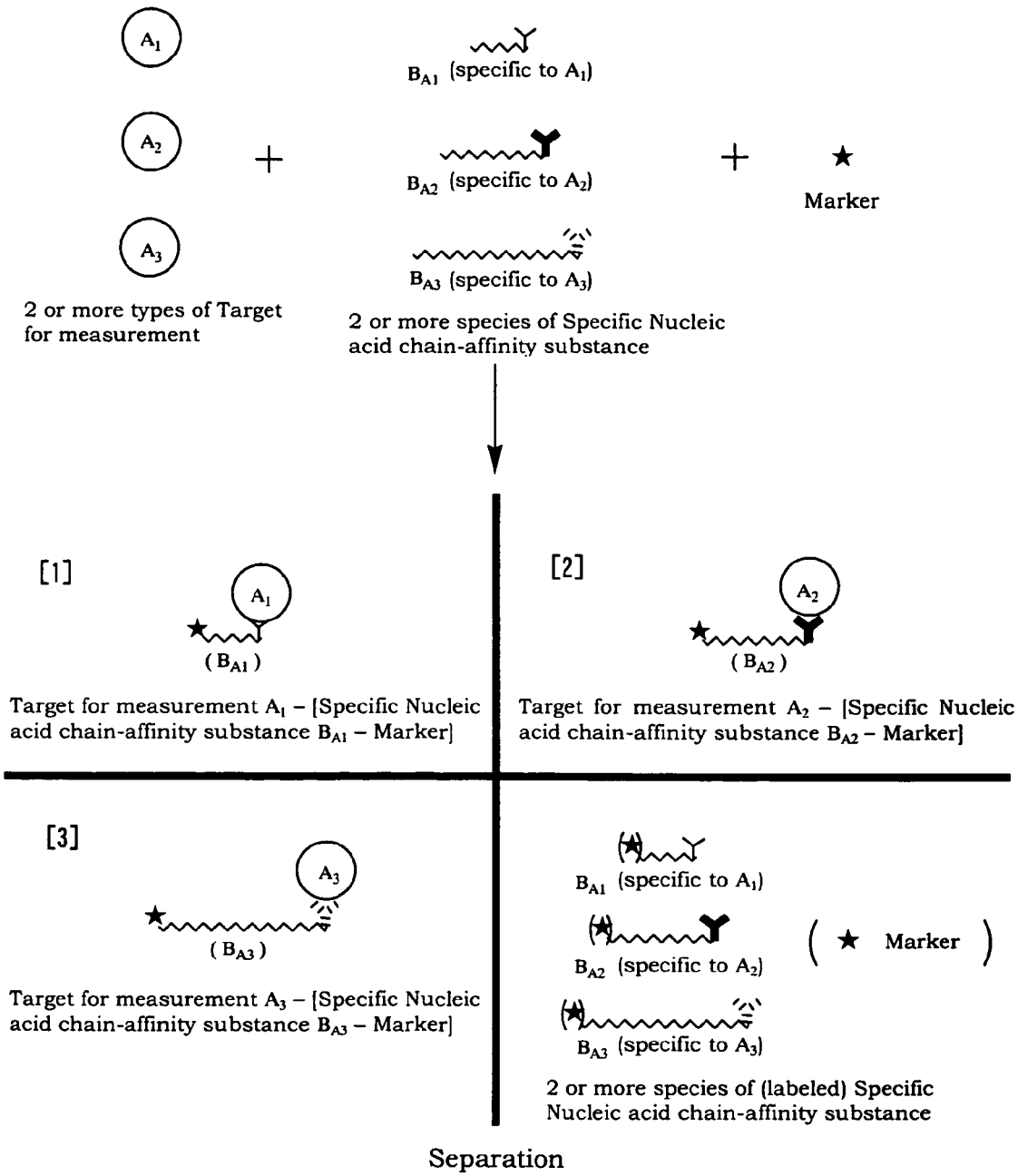
FIG. 6 shows schematically the separation method 4-b of the invention, that is, the principle how to vary the size (chain length) of specific nucleic acid chain-binding affinity substances to be bound to 2 or more types of targets for measurement respectively.

Next, a method for giving a difference in the nucleic acid chain length of the specific nucleic acid chain-binding affinity substances to be bound to 2 or more types of the targets for measurement is shown schematically in FIG. 6.

First, a sample containing 2 or more types of targets for measurement, 2 or more species of substances to which are bound nucleic acid chains of respectively different length and which have an affinity for only one type of the intended targets for measurement (specific nucleic acid chain-binding affinity substance), and a marker capable of labeling the nucleic acid chain, are formed into 2 or more species of complexes of the specific targets for measurement—the specific nucleic acid chain-binding affinity substances-marker, in which the nucleic acid length in the specific nucleic acid chain-binding affinity substance is different. Then, the complexes are respectively separated from the specific nucleic acid chain-binding affinity substance-markers not involved in the formation of the complexes, and if required from the marker by electrophoresis.

As 2 or more types of the targets for measurement separated in the above-mentioned method, similarly, the targets for measurement as mentioned above, i.e., the molecules containing 2 or more species of substances having the same action or molecules containing 2 or more species of substances having a similar structure but mutually different actions such as isozymes, isoforms, hormones, etc., are included. When there is a complex to which is bound only one species of the specific nucleic acid chain-binding affinity substance in a variety of the separated complexes, it is desirous for the above-mentioned targets for measurement that the pI in at least the target for measurement contained in the complex has the difference of 0.1 or more, preferably 0.5 or more, more preferably 1.0 or more, from the pH of the buffer used in electrophoretic separation.

In the above-mentioned method, the number of 2 or more types of the targets for measurement may be usually 2 or more, preferably 2 to 10, and more preferably 2 to 5, though there is no particular limitation.

As the nucleic acid chain in 2 or more species of substances to which are bound nucleic acid chains of respectively different length and which have an affinity for only one type of the intended targets for measurement (the specific nucleic acid chain-binding affinity substances) which are used in the above-mentioned method, the length of the nucleic acid chain may be designed so that 2 or more species of complexes of the specific targets for measurement—the specific nucleic acid chain-binding affinity substances-marker, in which the respective nucleic acid length is different in the mutually binding specific nucleic acid chain-binding affinity substances, can be separated from the specific nucleic acid chain-binding affinity substance-marker not involved in the formation of the complexes and if required from the marker. There is no particular limitation for separation. More specifically, for example, when n types of targets for measurement are separated with p species (p has the same meanings as mentioned above) of the specific nucleic acid chain-binding affinity substances, the relation between the nucleic acid chain contained in n species of the formed complexes and that contained in p species of the respective specific nucleic acid chain-binding affinity substances used may be represented by the followings. (1) (Among n species of the complexes and p species of the specific nucleic acid chain-binding affinity substances, the sum total of the nucleic acid chain length in the complex or the specific nucleic acid chain-binding affinity substance of which the total sum of the attached (bound) nucleic acid chain length is largest—the sum total of the nucleic acid chain length in the complex or the specific nucleic acid chain-binding affinity substance of which the total sum of the attached (bound) nucleic acid chain length is 2nd rank)/the sum total of the nucleic acid chain length in the complex or the specific nucleic acid chain-binding affinity substance of which the total sum of the attached (bound) nucleic acid chain length is largest; (2) (the sum total of the nucleic acid chain length in the complex or the specific nucleic acid chain-binding affinity substance of which the total sum of the attached (bound) nucleic acid chain length is 2nd rank—the sum total of the nucleic acid chain length in the complex or the specific nucleic acid chain-binding affinity substance of which the total sum of the attached (bound) nucleic acid chain length is 3rd rank)/the sum total of the nucleic acid chain length in the complex or the specific nucleic acid chain-binding affinity substance of which the total sum of the attached (bound) nucleic acid chain length is 2nd rank; ... ; and (n+p−1) [the sum total of the nucleic acid chain length in the complex or the specific nucleic acid chain-binding affinity substance of which the total sum of the attached (bound) nucleic acid chain length is n+p−1 rank—the sum total of the nucleic acid chain length in the complex or the specific nucleic acid chain-binding affinity substance of which the total sum of the attached (bound) nucleic acid chain length is n+p rank (smallest)]/the sum total of the nucleic acid chain length in the complex or the specific nucleic acid chain-binding affinity substance of which the total sum of the attached (bound) nucleic acid chain length is n+p−1 rank. In these formulae, the resulting value (X) is usually in the range of $0<X<1$, preferably $0.001 \leq X<1$, more preferably $0.01 \leq X<1$, further preferably $0.1 \leq X<1$, and particularly $0.5 \leq X<1$.

In the above-mentioned method, it is not necessary to consider the condition as mentioned above for separation of the respective free specific nucleic acid chain-binding affinity substances because the separation is unnecessary.

As the substances to which is bound a nucleic acid chain and which have an affinity for the specific target for measurement, those having an affinity only for the intended specific target separated may properly be chosen from the substances to which is bound a nucleic acid chain and which have an affinity for the target for measurement as mentioned above.

In the above-mentioned method, the number of the specific nucleic acid chain-binding affinity substances to be bound to the specific target for measurement is not necessary to be single, and 2 or more species may be used.

When 2 or more species of the specific nucleic acid chain-binding affinity substances are used, it is general to label all of them with a marker, but it is sufficient to label at least one species of the specific nucleic acid chain-binding affinity substances with a marker. The other species of the specific nucleic acid chain-binding affinity substances may be labeled or not with a marker.

In the above-mentioned method, the marker may be used alone or in a combination of 2 or more species. For example, the kinds of the marker may be varied according to the properties of the specific nucleic acid chain-binding affinity substance. In such a case, since the kinds of the markers are mutually different between the complexes of the specific targets for measurement—the specific nucleic acid chain-binding affinity substances-markers, it is possible to easily distinguish the formed complexes, i.e., the types of the targets for measurement.

In the above-mentioned method, the markers, the sample containing targets for measurement, the method for binding a nucleic acid chain to a substance having an affinity for the target for measurement, the method for labeling the nucleic acid chain with a marker, and the method for forming the complex are the same as mentioned above.

In the above-mentioned method, thus resulting 2 or more species of the complexes of the specific targets for measurement—the specific nucleic acid chain-binding affinity substances-marker, in which the nucleic acid chain length is different each other, are respectively separated from the specific nucleic acid chain-binding affinity substance-markers, and if required from the marker by electrophoresis. In this separation, a conventional method used in this field, so-called B/F separation procedure, can be applied in the same manner as mentioned above. Particularly, an electrophoretic method used in separation of proteins or nucleic acids is generally used, and capillary (chip) electrophoresis is preferred. The separating apparatuses, electric power sources for migration, buffers, fillers, a variety of reagents such as processing solutions, their concentration in using, the quality of a material for the capillary, conditions for separation (e.g., pH, temperature, applied voltage, time, and so on) are the same as mentioned above.

In the invention, the above-mentioned separation methods 1, 2, 3, 4, 4-a and 4-b may be carried out in a combination of 2 or more methods.

In the separation methods of the invention, using a complex of (specific) nucleic acid chain-binding affinity substance-marker together with a free substance having an affinity for the target for measurement and not binding to both of the nucleic acid chain and a marker (free binding affinity substance), it is allowable to form a complex comprising the free binding affinity substance, the target for measurement, and the (specific) nucleic acid chain-binding affinity substance-marker, a so-called sandwich complex {a complex of the free binding affinity substance—the target for measurement—[the (specific) nucleic acid chain-binding affinity substance-marker]}.

As the free binding affinity substance used in such a way, the same substances as mentioned above having an affinity for the target for measurement are exemplified, and, for example, the antibodies to the targets for measurement as mentioned above, lectin and the like may preferably be used. The formation of the complex of the free binding affinity substance— the target for measurement—[the (specific) nucleic acid chain-binding affinity substance-marker] may be carried out in the same manner as in the formation of the complex of the target for measurement—(the nucleic acid chain-binding affinity substance-marker).

The target for measurement separated by the separation method of the invention can be determined by a measuring method corresponding to the properties of the marker contained in the complex containing the target for measurement. Thus, the amount of the target for measurement contained in a sample can be determined based on the presence of the target for measurement in the sample or the amount of the resulting marker.

Briefly, the complex comprising the target for measurement, the substance to which is bound a nucleic acid chain and which has an affinity for the target for measurement (nucleic acid chain-binding affinity substance), and a marker capable of labeling the nucleic acid chain [complex of the target for measurement—(nucleic acid chain-binding affinity substance-marker)], are separated from the nucleic acid chain-binding affinity substance-marker not involved in the formation of the complex, and if required from the marker according to the separation method of the invention. The resulting complex may be measured by a measuring method corresponding to the properties of the marker contained in the complex. Thus, the amount of the target for measurement contained in a sample can be determined in high sensitivity and in a short period of time based on the presence of the target for measurement in the sample or the amount of the resulting marker.

The followings serve to illustrate in detail the cases in which the separation method 1, the separation method 2, the separation method 3, the separation method 4, the separation method 4-a and the separation method 4-b are utilized.

[Method for Measurement 1]

First, from a sample containing a target for measurement, one species of a substance to which is bound a nucleic acid chain and which has an affinity for the target for measurement (nucleic acid chain-binding affinity substance) and a marker capable of labeling the nucleic acid chain, a complex of the target for measurement—[the nucleic acid chain-binding affinity substance-marker] is prepared and separated from the nucleic acid chain-binding affinity substance-marker not involved in the formation of the complex, and if required from the marker according to the separation method 1 of the invention. Thus, the presence of the target for measurement in the sample can be determined by measuring the complex by a method corresponding to the properties of the marker contained in the complex. In addition, the amount of the target for measurement in the sample can be determined based on the amount of the marker thus obtained.

[Method for Measurement 2]

First, from a sample containing a target for measurement, 2 or more species of substances to which is bound a nucleic acid chain and which have an affinity for the target for measurement and respectively a different binding site, and a marker capable of labeling the nucleic acid chain, complexes of the target for measurement —[2 or more species of the nucleic acid chain-binding affinity substance-markers] are prepared and separated from the 2 or more species of nucleic acid chain-binding affinity substance-marker not involved in the formation of the complexes, and if required from the marker according to the separation method 2 of the invention. Thus, the presence of the target for measurement in the sample can be determined for measurement by measuring the complex by a method corresponding to the properties of the marker contained in the complex. In addition, the amount of the target for measurement in the sample can be determined based on the amount of the marker thus obtained.

[Method for Measurement 3]

First, from (a) a sample containing mutually different n types of targets $A_1, A_2, A_3, \ldots, A_{n-1}$ and $A_n$ for measurement, (b)(1) a substance to which is bound a nucleic acid chain and which has an affinity to all of the targets $A_1$ to $A_n$ for measurement (nucleic acid chain-binding affinity substance $B_{A1:An}$), (2) a substance to which is bound a nucleic acid chain and which has an affinity to all of the targets $A_2$ to $A_n$ for measurement except for $A_1$ (nucleic acid chain-binding affinity substance $B_{A2:An}$), (3) a substance to which is bound a nucleic acid chain and which has an affinity to all of the targets $A_3$ to $A_n$ for measurement except for $A_1$ and $A_2$ (nucleic acid chain-binding affinity substance $B_{A3:An}$), . . . , (n−1) a substance to which is bound a nucleic acid chain and which has an affinity to the targets $A_{n-1}$ and $A_n$ for measurement except for all of $A_1$ to $A_{n-2}$ (nucleic acid chain-binding affinity substance $B_{An-1:An}$), and (n) a substance to which is bound a nucleic acid chain and which has an affinity only to the target $A_n$ for measurement except for all of $A_1$ to $A_{n-1}$ (nucleic acid chain-binding affinity substance $B_{An}$), and (c) a marker capable of labeling said nucleic acid chain, [1] a complex of the target $A_1$ for measurement—nucleic acid chain-binding affinity substance $B_{A1:An}$—marker, [2] a complex of the target $A_2$ for measurement—nucleic acid chain-binding affinity substance $B_{A1:An}$ and nucleic acid chain-binding affinity substance $B_{A2:An}$—marker, [3] a complex of the target $A_3$ for measurement—nucleic acid chain-binding affinity substance $B_{A1:An}$, nucleic acid chain-binding affinity substance $B_{A2:An}$ and nucleic acid chain-binding affinity substance $B_{A1:An}$—marker, . . . , [n−1] a complex of the target $A_{n-1}$ for measurement—nucleic acid chain-binding affinity substance $B_{A1:An}$, nucleic acid chain-binding affinity substance $B_{A2:An}$, nucleic acid chain-binding affinity substance $B_{A3:An}$, . . . and nucleic acid chain-binding affinity substance $B_{An-1:An}$—marker, and [n] a complex of the target $A_n$ for measurement—nucleic acid chain-binding affinity substance $B_{A1:An}$, nucleic acid chain-binding affinity substance $B_{A2:An}$, nucleic acid chain-binding affinity substance $B_{A3:An}$, . . . nucleic acid chain-binding affinity substance $B_{An-1:An}$ and nucleic acid chain-binding affinity substance $B_{An}$—marker, are prepared and then separated from complexes of the respective nucleic acid chain-binding affinity substances (1) to (n) and the marker not involved in the formation of these complexes [1] to [n] and if required from the markers according to the separation method 3 of the invention. Thus, the presence of n types of the mutually different targets $A_1, A_2, A_3, A_{n-1}$ and $A_n$ for measurement contained in the sample can be determined by measuring the respective complexes by a method corresponding to the properties of the marker contained in the respective complexes [1] to [n]. In addition, the amount of the target for measurement in the sample can also be determined based on the amount of the marker thus obtained.

[Method for Measurement 4]

From a sample containing 2 or more types of targets for measurement, 2 or more species of substances to which is bound a nucleic acid chain and which have an affinity for only one of the intended targets for measurement (specific nucleic acid chain-binding affinity substances), and a marker capable of labeling the nucleic acid chain, 2 or more species of complexes comprising the specific targets for measurement—the specific nucleic acid chain-binding affinity substances—the marker are prepared and separated from the specific nucleic acid chain-binding affinity substance-markers not involved in the formation of the complexes, and if required from the marker according to the separation method 4 of the invention. Thus, the presence of 2 or more types of the targets for measurement in the sample can be determined by measuring 2 or more species of the complexes comprising the specific targets for measurement—the specific nucleic acid chain-binding affinity substances—the marker by a method corresponding to the properties of the marker contained in the respective complexes. In addition, the amount of the target for measurement in the sample can be determined based on the amount of the marker thus obtained.

[Method for Measurement 4-a]

From a sample containing 2 or more types of targets for measurement in which the number of the binding site for the substances having an affinity for the targets for measurement is different, 2 or more species of substances to which is bound a nucleic acid chain and which have an affinity for only one of the intended targets for measurement (specific nucleic acid chain-binding affinity substances), and a marker capable of labeling the nucleic acid chain, 2 or more species of complexes comprising the specific targets for measurement—the specific nucleic acid chain-binding affinity substances—the marker, in which the number of the mutually binding specific nucleic acid chain-binding substances is different, are prepared and respectively separated from the specific nucleic acid chain-binding affinity substance-markers not involved in the formation of the complexes, and if required from the marker according to the separation method 4-a of the invention. Thus, the presence of 2 or more types of the targets for measurement, in which the number of the binding sites capable of binding to a substance having an affinity only for the respective targets for measurement in the sample is different, the mutually binding specific nucleic acid chain-binding substances is different, can be determined by measuring 2 or more species of the complexes comprising the specific targets for measurement—the specific nucleic acid chain-binding affinity substances—the marker, in which the number of the mutually binding specific nucleic acid chain-binding substances is different, by a method corresponding to the properties of the marker contained in the respective complexes. In addition, the amount of the target for measurement in the sample can be determined based on the amount of the marker thus obtained.

[Method for Measurement 4-b]

First, from a sample containing 2 or more types of targets for measurement, 2 or more species of substances to which are bound nucleic acid chains of respectively different length and which have an affinity for only one type of the intended targets for measurement (specific nucleic acid chain-binding affinity substance), and a marker capable of labeling the nucleic acid chain, 2 or more species of complexes of the specific targets for measurement—the specific nucleic acid chain-binding affinity substances-marker in which the nucleic acid length in the specific nucleic acid chain-binding affinity substance is different, are prepared, and respectively separated from the specific nucleic acid chain-binding affinity substance-markers not involved in the formation of these complexes, and if required from the marker according to the separation method 4-b of the invention. Thus, the presence of 2 or more types of the targets for measurement in the sample can respectively be determined by measuring 2 or more species of the complexes comprising the specific targets for measurement—the specific nucleic acid chain-binding affinity substances—the marker, in which the nucleic acid length in the respectively binding specific nucleic acid chain-binding affinity substance is different, by a method corresponding to the properties of the marker contained in the respective complexes. In addition, the amount of the target for measurement in the sample can be determined based on the amount of the marker thus obtained.

In the above-mentioned method, in determining the amount of the target for measurement in a sample based on the amount of the marker of the resulting complex, for example, another sample containing the target for measurement at a known concentration is used in the same measurement condition as mentioned above to prepare a calibration curve showing a relationship between the amount of the target for measurement thus obtained and that of the marker in the complex. To this calibration curve is adapted the measured value of the marker obtained by measurement of a sample containing the target for measurement to determine the amount of the intended target for measurement.

In addition, it is possible to calculate the relative amount of the target for measurement contained in a sample by adding a detectable substance as an internal standard at a known concentration to a sample, followed by comparison of the amount of the substance added as an internal standard with that of the marker contained in the complex. In such a way, it becomes possible to correct the error between electrophoretic apparatuses.

In the above-mentioned method, as the detectable substance, it is general to use nucleic acid chains labeled with a marker as mentioned above.

In the method of the invention, measurement of the marker contained in a variety of complexes separated may be achieved according to a conventional manner responding to the type of the marker used. For example, when the property of the marker depends on an enzymatic activity, the measurement may be conducted in a conventional way of EIA or hybridization as described in, for example, "Enzyme Immunoassay" Protein, Nucleic Acid and Enzyme, Supplementary Volume 31, Edited by Tsunehiro Kitagawa, Toshio Nambara, Akio Tuji, and Eiji Ishikawa, pages 51-63, Kyoritsu Shuppan Co., Ltd., Published on Sep. 10, 1987. When the marker is a radioactive material, it may be detected according to a conventional way of RIA or hybridization using a suitable detector such as a dipping-type GM counter, liquid scintillation counter, well-type scintillation counter, etc., responding to the kind and strength of the radiation emitted by the radioactive material [see: Ikagaku Jikken Koza (Experimental Manual in Medical Chemistry), vol. 8, Edited by Yuichi Yamamura, First edition, Nakayama Shoten, 1971; Seikagaku Jikkenn Koza (Experimental Manual in Biochemistry), 2, Experimental Procedure for Tracer, Last Volume, Akihiro Takemura, Tasuku Honjo, pages 501-525, Tokyo Kagaku Dojin, Published on Feb. 25, 1977]. When the property of the marker depends on fluorescence, the measurement may be conducted in a conventional way of FIA or hybridization using a detector such as a fluorophotometer or confocal laser microscope as described in Zusetu (Illustrative Description) Fluorescent Antibodies, Akira Kawao, First Edition, Soft Science, 1983; Seikagaku Jikkenn Koza (Experimental Manual in Biochemistry), 2, Chemistry of Nucleic Acid III, Mineo Saneyoshi, pages 299-318, Tokyo Kagaku Dojin, Published on Dec. 15, 1977. When the property of the marker depends on luminescence, the measurement may be conducted in a conventional way using a detector such as a photon counter according to a method as described in, for example, "Enzyme Immunoassay" Protein, Nucleic Acid and Enzyme, Supplementary Volume 31, Edited by Tsunehiro Kitagawa, Toshio Nambara, Akio Tuji, and Eiji Ishikawa, pages 252-263, Kyoritsu Shuppan Co., Ltd., Published on Sep. 10, 1987. Further, when the property is of absorbance in an ultraviolet region, detection may be conducted in a conventional way using a detector such as a spectrophotometer. When the property is of coloring, the detection may be conducted in a conventional way using a detector such as a spectrophotometer or microscope. In addition, when the analyte has a property of spin, the detection may be conducted in a conventional way using a detector such as an electron spin resonance apparatus according to a method as described in, for example, "Enzyme Immunoassay" Protein, Nucleic Acid and Enzyme, Supplementary Volume 31, Edited by Tsunehiro Kitagawa, Toshio Nambara, Akio Tuji, and Eiji Ishikawa, pages 264-271, Kyoritsu Shuppan Co., Ltd., Published on Sep. 10, 1987.

The method for measurement in the invention may be conducted according to the above-mentioned per se known methods using reagents properly chosen in a per se conventional manner except utilizing the separation method of the invention.

In the method for measurement in the invention, the above-mentioned measurement methods 1, 2, 3, 4, 4-a and 4-b may be used in a combination of 2 or more.

In carrying out the separation method and the measurement method of the invention, when there is a possibility of the existence of a nuclease or nucleases such as DNase, RNase, etc., it is appropriate to add a nuclease inhibitor such as ethylene glycol bis(2-aminoethyl ether)tetraacetate (EGTA), ethylenediamine tetraacetate (EDTA), heparin, and the like to a liquid containing a nucleic acid chain (including the nucleic acid chain contained in a nucleic acid chain-binding affinity substance or a complex of a nucleic acid chain-binding affinity substance and a target for measurement, or a complex comprising a nucleic acid chain, a target for measurement and a marker).

Briefly, when the nucleic acid chain (including the nucleic acid chain contained in a nucleic acid chain-binding affinity substance or a complex of a nucleic acid chain-binding affinity substance and a target for measurement) is made contact with another substance [for example, when the nucleic acid chain (including the nucleic acid chain contained in a nucleic acid chain-binding affinity substance or a complex of a nucleic acid chain-binding affinity substance and a target for measurement) is made contact with a sample containing a target for measurement, or when the nucleic acid chain is made contact with a substance having an affinity for the target for measurement, or when the nucleic acid chain (including the nucleic acid chain contained in a nucleic acid chain-binding affinity substance) is labeled with a marker, or when the nucleic acid chain is formed into a complex with a target for measurement and a marker, and so on] or when a complex of a nucleic acid chain, target for measurement and marker is separated from the nucleic acid chain-binding affinity substance-marker not involved in the formation of the complex and if required from the marker, it is appropriate to add an inhibitor as mentioned above to a liquid containing the nucleic acid chain (including the nucleic acid chain contained in a nucleic acid chain-binding affinity substance or a complex of a nucleic acid chain-binding affinity substance and a target for measurement or a complex comprising a nucleic acid chain, a target for measurement and a marker) or a liquid which is made contact with the nucleic acid chain in order to carry out the contact in the presence of the inhibitor.

The reagents, etc., used for conducting the present invention may be formulated into a kit for electrophoretic measurement of a target or targets so that the above-mentioned method of the invention can successively be carried out.

Specifically, the kit for measurement of a target or targets of the invention comprises a substance to which is bound a nucleic acid chain and which has an affinity for the target for measurement and a marker capable of labeling the nucleic acid chain. The preferred embodiment or examples of the respective components are as mentioned above.

In the kit of the invention, it is particularly advantageous to label a substance to which is bound a nucleic acid chain and which has an affinity for the target for measurement in advance with a marker capable of labeling the nucleic acid chain since the step for labeling of the substance with the marker can be omitted.

The above-mentioned kit may be used in a combination with an electrophoretic apparatus, particularly, capillary electrophoretic apparatus.

The invention will be explained more specifically by the following Examples and Comparative Examples which are not intended to limit the scope of the invention.

EXAMPLES

Comparative Example 1

Detection of AFP Using Capillary Chip Electrophoresis in a Conventional Method

[Target for Measurement (Antigen)]
α-Fetoprotein (Wako Pure Chemical Industries, Ltd.)

[Antibodies]
Using 3 types of anti-AFP antibodies, WA2, A4-4 and WA1 (all available from Wako Pure Chemical Industries, Ltd.), which recognize respectively different epitopes of AFP, the antibodies used in this example were prepared as follows.

YS5-labeled WA2 Fab' antibody: Using anti-AFP antibody WA2, an anti-AFP antibody Fab' fragment to which had been bound a peptide chain (YS5) having 5 sulfated tyrosine residues (YS5-labeled WA2 Fab' antibody) was prepared according to the method as described in Japanese Patent Laid-Open No. 301995/1997.

YS8-labeled A4-4 Fab' antibody: In the same manner as mentioned above, using anti-AFP antibody A4-4, an anti-AFP antibody Fab' fragment) to which had been bound a peptide chain (YS8) having 8 sulfated tyrosine residues (YS8-labeled A4-4 Fab' antibody was prepared according to the method as described in Japanese Patent Laid-Open No. 301995/1997.

Alexa488-labeled WA1 Fab' antibody: Anti-AFP antibody WA1 was processed in a conventional manner to give a Fab' fragment, into which was introduced a fluorescent substance Alexa488 (Molecular Probes, Inc.) on the amino group in a conventional manner to give an Alexa488-labeled anti-AFP antibody Fab' fragment (Alexa488-labeled WA1 Fab' antibody).

[Samples]
A variety of specified antibodies described in Table 1 were allowed to react as a mixture with AFP in a specified concentration, and dissolved in an ACES buffer [50 mM N-(2-acetamido)-2-aminoethanesulfonic acid (ACES), pH 7.5] to use as samples. When the samples were subjected to electrophoresis, they were diluted 10-fold with a buffer used in electrophoresis. Further, when the plural samples were used as a mixture in electrophoresis, the respective samples were mixed and diluted immediately before applying to electrophoresis.

TABLE 1

| Sample No. | YS5 antibody 11.3 µM | YS8 antibody 11.3 µM | AFP 11.3 µM | Alexa488 antibody 11.3 µM | Isoelectric point |
|---|---|---|---|---|---|
| 1 | + | + | + | + | 5.2 ± 0.5 smear |
| 2 | + | − | + | + | 4.9 ± 0.3 smear |
| 3 | − | + | + | + | 4.5 ± 0.2 smear |
| 4 | − | − | + | + | around 4.5 smear |
| 5 | − | − | − | + | around 7.35 smear |

[Condition for Electrophoresis]
As an electrophoretic apparatus, a capillary electrophoretic apparatus "Hitachi SV1100 Cosmo AI" (a product of Hitachi Chemical Co., Ltd.). As a capillary chip, a kit i-chip for analyzing a DNA chain length (Hitachi Chemical Co., Ltd.) provided for a Hitachi SV1100 Microchip Electrophoretic Apparatus Cosmo AI was used.

In carrying out electrophoresis, an electrophoretic buffer as mentioned below was filled in a capillary chip, into which was introduced a sample. Then, a specific voltage was applied thereto to start electrophoresis using a power source specially ordered for electrophoresis (Apple Electronics).

Figure 7:
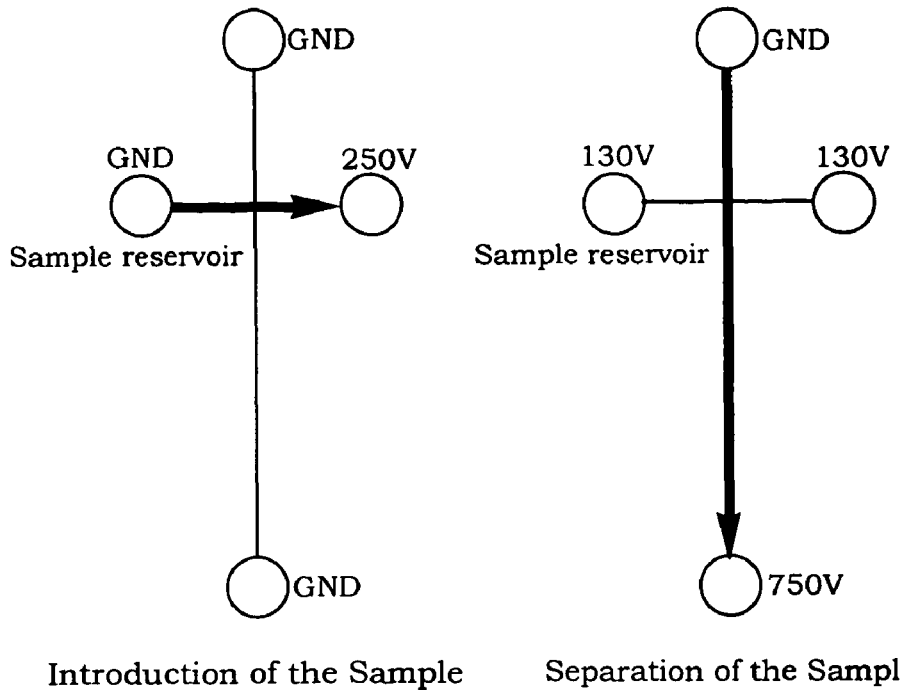
FIG. 7 schematically shows an electrophoretic apparatus used in Comparative Example 1.

FIG. 7 shows a diagrammatic sketch of an electrophoretic apparatus used.

Introduction of a sample: 40 seconds
Separation of the sample: 120 seconds
Applied voltage: as shown in FIG. 7

In this operation, the detection was made immediately from starting of the sample separation with a lapse of time by measuring through photomultiplication of fluorescence excited with a xenon lamp the fluorescence intensity at the part 3 cm apart from the capillary-crossing point using a fluorescence microscope (BX-50; KS Olympus Co., Ltd.).

Electrophoretic buffer: 50 mM Tris-borate buffer (pH 8.0)

[Results]

Figure 8:
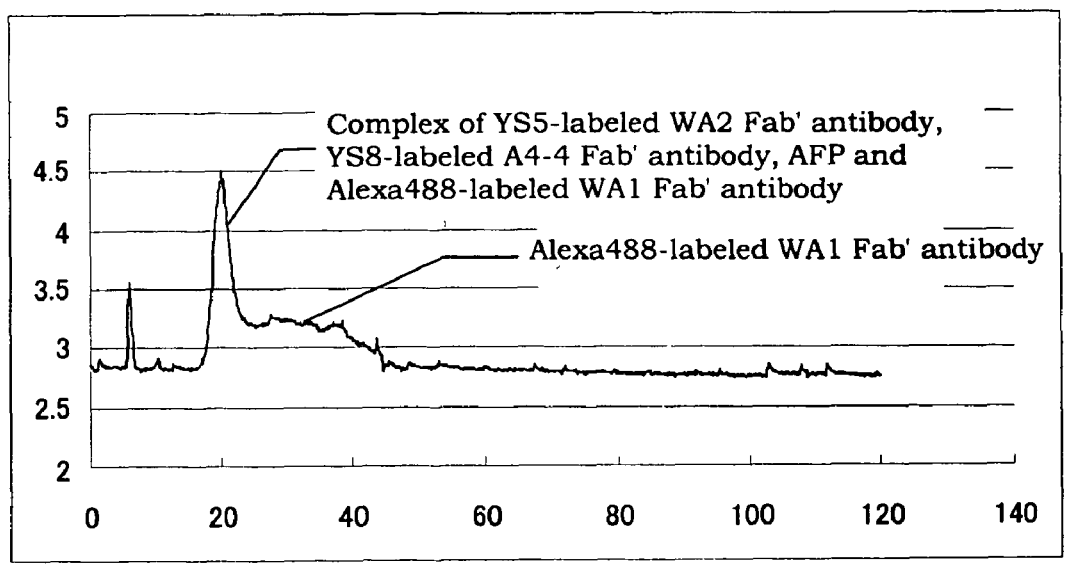
FIG. 8 shows the result (capillary chip electrophoretic chromatogram) of electrophoresis for a mixture of Sample 1 and Sample 5 (containing a complex of YS5-labeled WA2 Fab' antibody—YS8-labeled A4-4 Fab' antibody—AFP—Alexa488-labeled WA1 Fab' antibody, and a free Alexa488-labeled WA1 Fab' antibody) obtained in Comparative Example 1.
Figure 9:
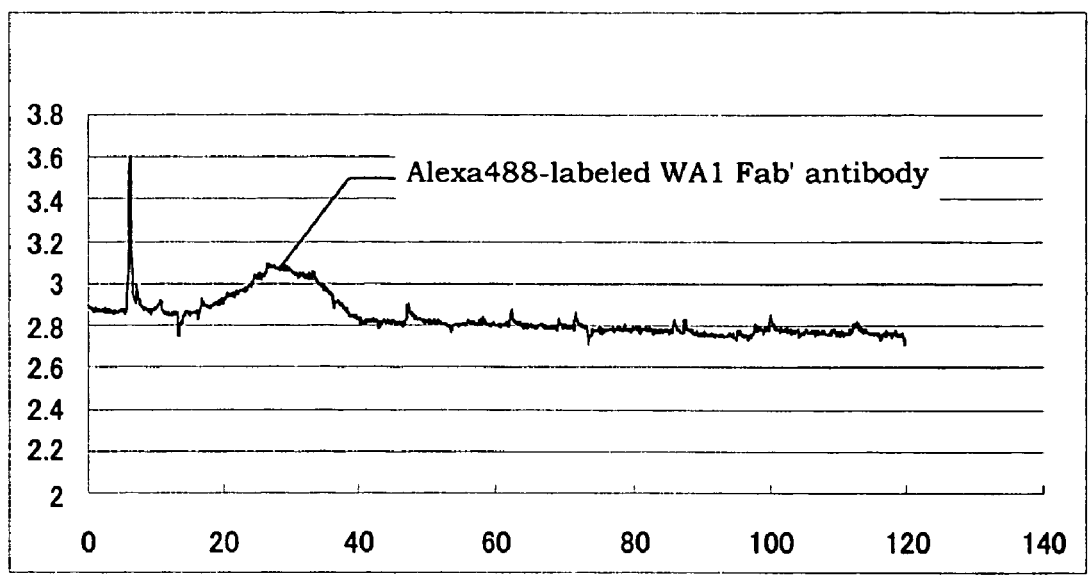
FIG. 9 shows the result (capillary chip electrophoretic chromatogram) of electrophoresis for Sample 5 (containing Alexa488-labeled WA1 Fab' antibody alone) obtained in Comparative Example 1.

FIG. 8 shows the results of electrophoresis (capillary-chip electrophoretic chromatogram) on a mixture of Sample 1 and Sample 5 (containing a complex of YS5-labeled WA2 Fab' antibody—YS8-labeled A4-4 Fab' antibody—AFP—Alexa488-labeled WA1 Fab' antibody, and a free Alexa488-labeled WA1 Fab' antibody). FIG. 9 shows the result for Sample 5 (containing only Alexa488-labeled WA1 Fab' antibody).

As apparent from FIG. 8 and FIG. 9, it was found that when Sample 1+Sample 5 were used, two peaks, that is, a broad peak of retarded retention time corresponding to the free Alexa488-labeled WA1 Fab' antibody and a peak of short retention time corresponding to the complex of YS5-labeled WA2 Fab' antibody-YS8-labeled A4-4 Fab' antibody-AFP-Alexa488-labeled WA1 Fab' antibody were recognized, but their separation was insufficient because two peaks were overlapped halfway through the peaks.

Moreover, when Sample 2+Sample 5, Sample 3+Sample 5, and Sample 4+Sample 5 were used, the complex could not separated distinctly from the free antibody, too.

In addition, the concentration of the electrophoretic buffer was changed into 5 mM Tris-borate (pH8.0) to decrease the concentration of buffering agent and the detection was conducted in the same manner. The peak of the complex and the peak of the free antibody, however, were not sufficiently separated and this method for separation was judged practically insufficient, accordingly.

Example 1

Separation and Detection of Proteins by Capillary-Chip Electrophoresis Using DNA

[Target for Measurement (Antigen)]

In the same manner as in Comparative Example 1, AFP was used as a target for measurement.

[Antibodies]

An anti-AFP antibody Fab' fragment to which was bound DNA was prepared according to the procedure as shown in the following Table 2.

Briefly, 160 bp and 227 bp DNA fragments into which had been introduced an $NH_2$ group at the 5' end were purified in a conventional manner, and the $NH_2$ group introduced to these DNA fragments were allowed to react with the succinimido group of a sulfosuccinimidyl 4-(p-maleimidophenyl)butyrate (Sulfo-SMPB) linker (linker having a succinimido group and a maleimido group; Pierce chemical Co.) in a conventional manner. The product was applied to gel filtration to remove un-reacted linker yielding DNA fragments (160 bp and 227 bp), which had respectively been bound to the linker. Thus resulting linker-binding 227 bp DNA fragment was allowed to react with an anti-AFP antibody WA2 Fab' fragment which had been prepared from an anti-AFP antibody WA2 (Wako Pure Chemical Industries, Ltd.) beforehand. In addition, the similarly prepared linker-binding 160 bp DNA fragment was allowed to react with a Fab' fragment which had been prepared from an anti-AFP antibody A4-4 (Wako Pure Chemical Industries, Ltd.). The respective products were purified with a DEAE column to give an anti-AFP antibody WA2 Fab' fragment binding to the 227 bp DNA fragment (227WA2 antibody) and an anti-AFP antibody A4-4 Fab' fragment binding to the 160 bp DNA fragment (160A4-4 antibody), respectively.

[Samples]

A variety of specific antibodies were mixed and reacted with AFP at a specified concentration as described in Table 3 in an ACES buffer [50 mM N-(2-acetamido)-2-aminoethane-sulfonic acid (ACES), pH 7.5] to use as samples as solutions.

In carrying out electrophoresis, the respective samples were diluted 10-fold with an electrophoretic buffer containing 0.5 μg/ml of ethidium bromide. Further, when the plural samples were used as a mixture in electrophoresis, the respective samples were mixed and diluted with said buffer immediately before applying to electrophoresis. As internal standards, a 100 bp double-strand DNA was added to the sample at 31 nM and/or a 800 bp double-strand DNA was added at 3.9 nM. In addition, as controls, a 160 bp DNA fragment not binding to any antibody was added to the sample at 194 nM and/or a 227 bp DNA fragment was added at 136 nM. In this procedure, the internal standard and the control were mixed with the sample immediately before applying to electrophoresis.

TABLE 2

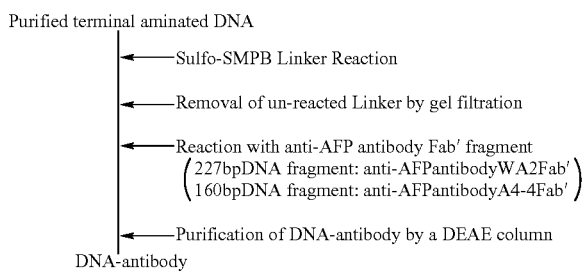

TABLE 3

| Sample No. | 227WA2 antibody 15 nM | 160A4-4 antibody 20 nM | AFP 20 nM |
|---|---|---|---|
| 1 | + | − | − |
| 2 | − | + | − |
| 3 | + | − | + |
| 4 | − | + | + |
| 5 | + | + | − |
| 6 | + | + | + |

[Condition for Electrophoresis]

The same electrophoretic apparatus and capillary chip as in Comparative Example 1 were used.

Introduction of a sample: 40 seconds

Separation of the sample: 180 seconds

Applied voltage: the same as in Comparative Example 1

In this operation, the detection was made immediately from starting of the sample separation with a lapse of time by measuring with a xenon lamp LED-photodiode the fluorescence intensity at the part 3 cm apart from the capillary-crossing point using a fluorescence microscope (BX-50; KS Olympus Co., Ltd.).

Electrophoretic buffer: a buffer attached to a kit i-chip for analyzing a DNA length (Hitachi Chemical Co., Ltd.) provided for a Hitachi SV1100 Microchip Electrophoretic Apparatus Cosmo AI.

[Results]

Figure 10:
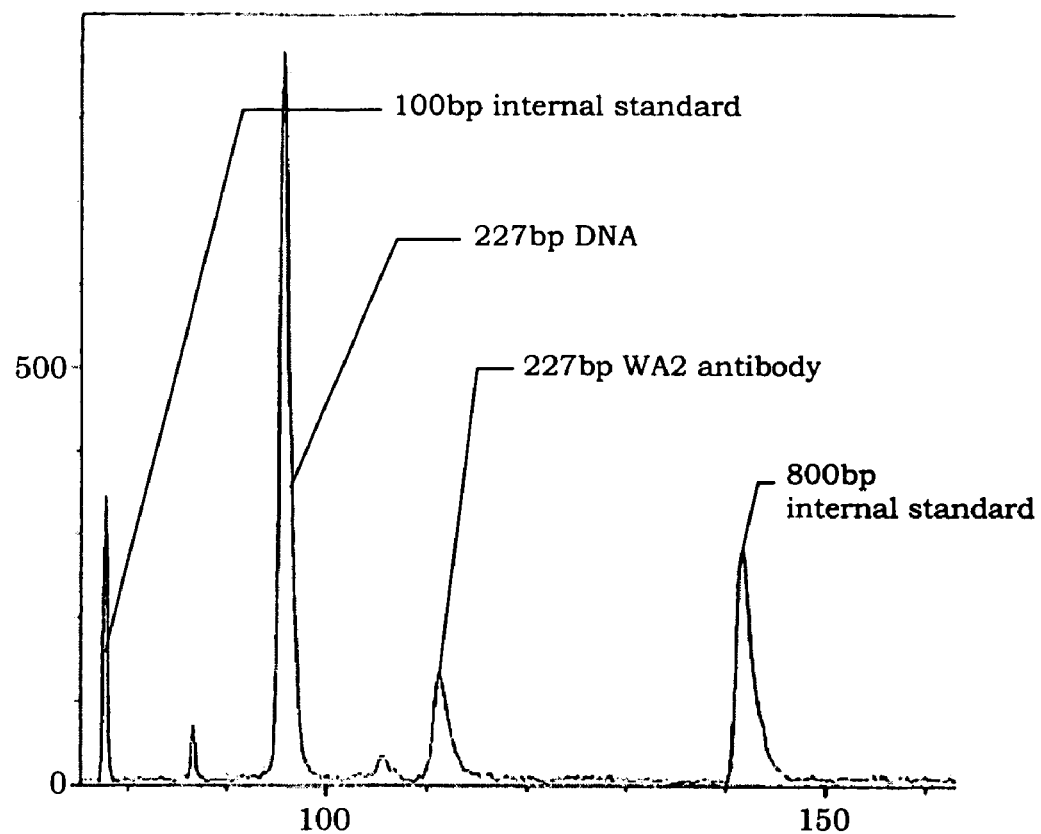
FIG. 10 shows the result (capillary chip electrophoretic chromatogram) of electrophoresis for Sample 1 (containing 227 bpWA2 antibody) obtained in Example 1.
Figure 11:
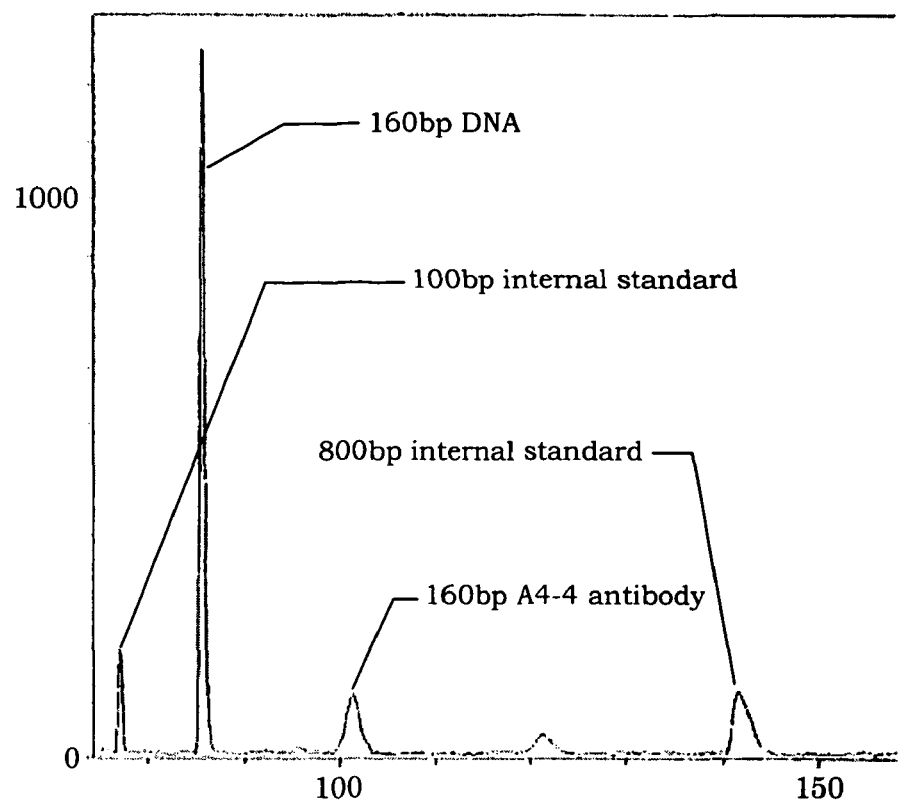
FIG. 11 shows the result (capillary chip electrophoretic chromatogram) of electrophoresis for Sample 2 (containing 160 bpA4-4 antibody) obtained in Example 1.
Figure 12:
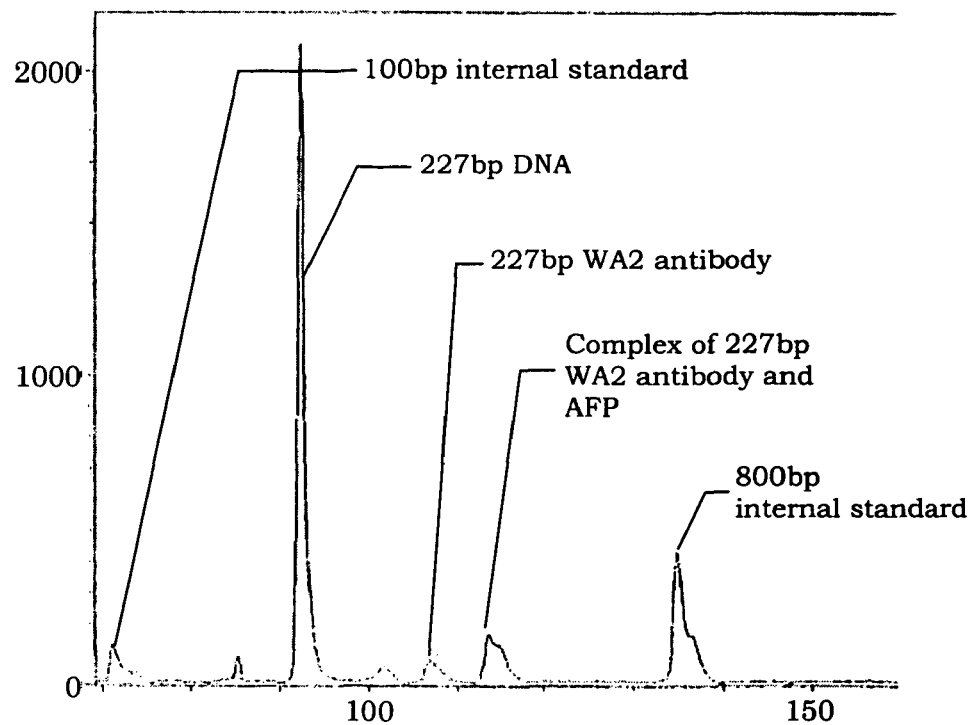
FIG. 12 shows the result (capillary chip electrophoretic chromatogram) of electrophoresis for a mixture of Sample 1 and Sample 3 (containing 227 bpWA2 antibody and a 227 bpWA2 antibody—AFP complex) obtained in Example 1.
Figure 13:
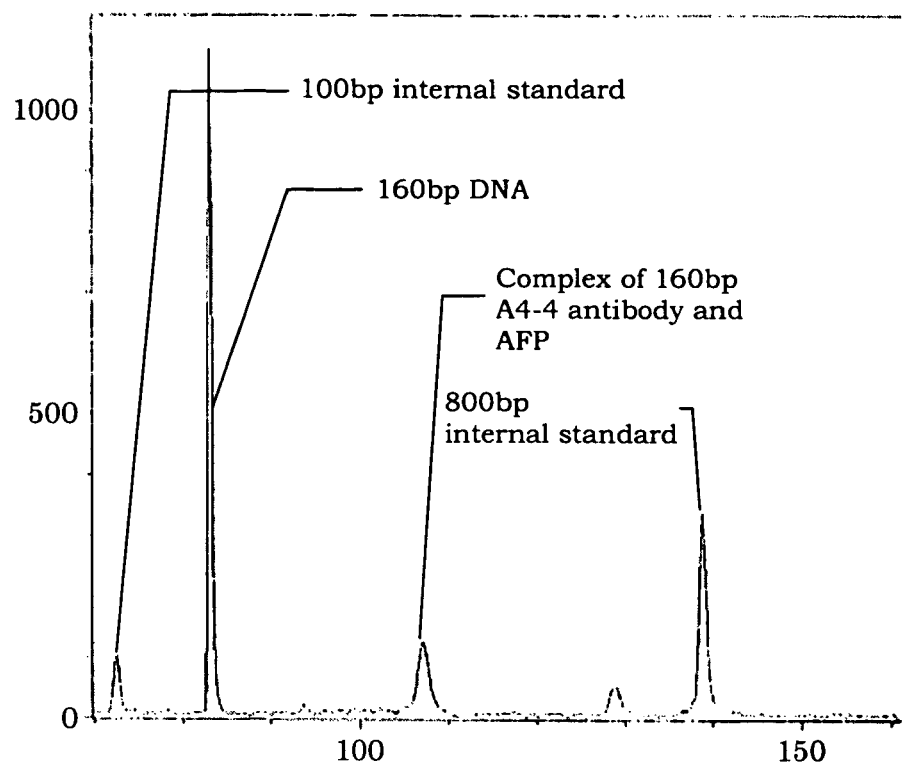
FIG. 13 shows the result (capillary chip electrophoretic chromatogram) of electrophoresis for Sample 4 (containing a 160 bpA4-4 antibody—AFP complex) obtained in Example 1.
Figure 14:
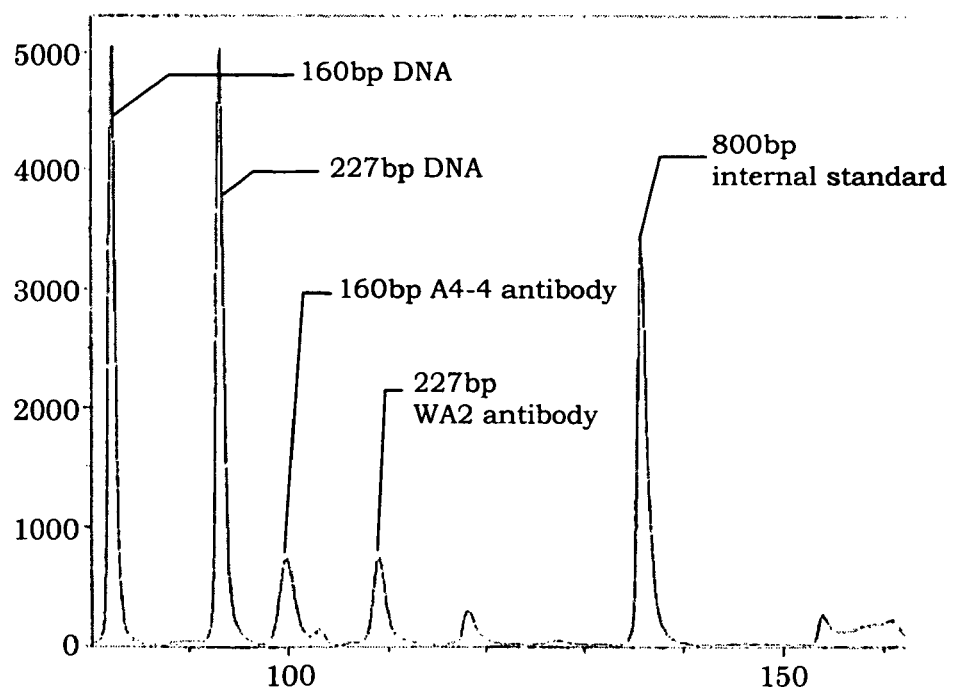
FIG. 14 shows the result (capillary chip electrophoretic chromatogram) of electrophoresis for Sample 5 (containing 227 bpWA2 antibody and 160 bpA4-4 antibody) obtained in Example 1.
Figure 15:
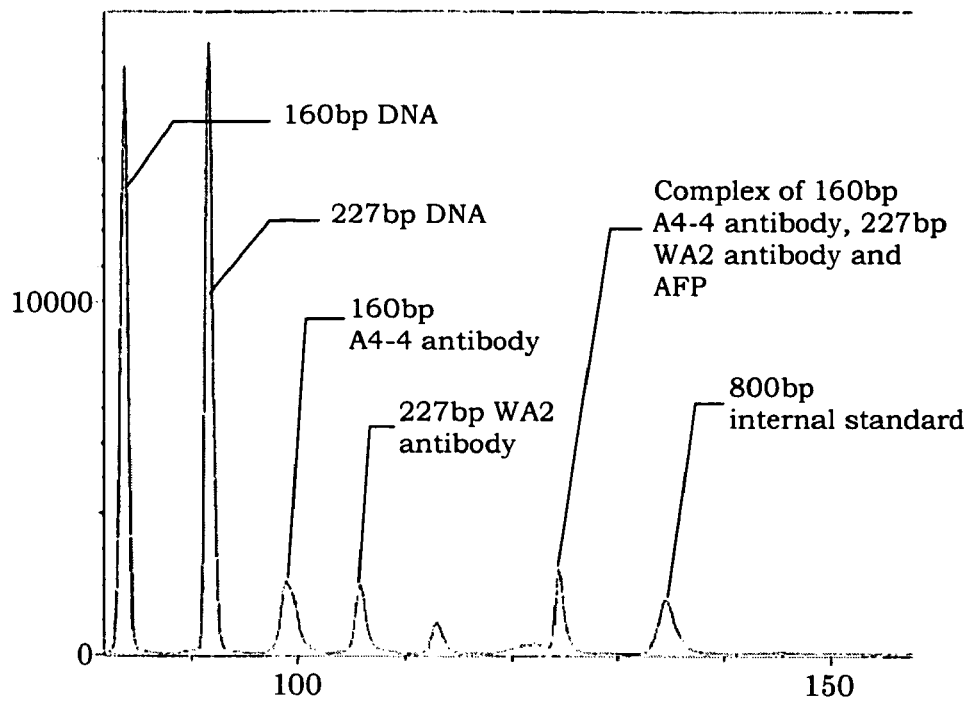
FIG. 15 shows the result (capillary chip electrophoretic chromatogram) of electrophoresis for a mixture of Sample 6 and Sample 5 (containing a 227 bpWA2 antibody-160 bpA4-4 antibody—AFP complex, and a free 227 bpWA2 antibody and a free 160 bpA4-4 antibody) obtained in Example 1.

FIG. 10 shows the result (capillary-chip electrophoretic chromatogram) of electrophoresis for Sample 1 (containing a 227 bp WA2 antibody). FIG. 11 shows the result (capillary-chip electrophoretic chromatogram) of electrophoresis for Sample 2 (containing a 160 bp A4-4 antibody). FIG. 12 shows the result (capillary-chip electrophoretic chromatogram) of electrophoresis for a mixture of Sample 1 and Sample 3 (containing a free 227 bp WA2 antibody and a 227 bp WA2 antibody-AFP complex). FIG. 13 shows the result (capillary-chip electrophoretic chromatogram) of electrophoresis for Sample 4 (containing a 160 bp A4-4 antibody-AFP complex). FIG. 14 shows the result (capillary-chip electrophoretic chromatogram) of electrophoresis for Sample 5 (containing a 227 bp WA2 antibody and a 160 bp A4-4 antibody). FIG. 15 shows the result (capillary-chip electrophoretic chromatogram) of electrophoresis for a mixture of Sample 6 and Sample 5 (containing a 227 bp WA2 antibody-160 bp A4-4 antibody-AFP complex, and a free 227 bp WA2 antibody and a free 160 bp A4-4 antibody).

From the results as shown in FIG. 10 and FIG. 12, it is understood that the binding of AFP to the 227WA2 antibody (formation of the complex) prolongs the retention time compared with that of the 227WA2 antibody alone. And from the results as shown in FIG. 13 and FIG. 14, it is understood that the binding of AFP to the 160A4-4 antibody prolongs the retention time compared with that of the 160A4-4 antibody alone. From the above facts, it is understood that, in the method for separation of the invention, formation of a complex comprising a target for measurement, a nucleic acid chain-binding affinity substance and a marker allows efficient separation of said complex from a complex of the nucleic acid chain-binding affinity substance and the marker not involved in the formation of said complex in a short period of time, said complex being formed by binding to the target for measurement a substance (nucleic acid chain-binding affinity substance) which has an affinity for the target for measurement and is labeled with a marker and bound to a nucleic acid chain.

As seen from FIG. 12 and FIG. 13, it is understood that the 160 bp A4-4 antibody-AFP complex and the 227 bp WA2 antibody-AFP complex are different in their retention time. In other words, it is understood that variation of the chain length of nucleic acid allows optional control of the retention time of the formed complex. Moreover, as for 2 or more types of targets for measurement, the retention time of a complex containing 2 or more types of targets for measurement can be varied by binding respectively different length of nucleic acid chains. It is also understood, accordingly, that 2 or more types of targets for measurement can be measured at the same time.

Moreover, as seen from the results of FIG. 14 and FIG. 15, a complex formed from 3 components, i.e., AFP, 160 bp A4-4 antibody and 227 bp WA2 antibody, has more retardant retention time than the complex of 160 bp A4-4 and AFP (FIG. 13) or of 227 bp WA2 and AFP (FIG. 12). In other words, it is understood that the complexes can be separated more exactly. That is, it is understood that binding of multiple affinity substances binding to nucleic acid chains to the target for measurement allows further improvement of resolution.

Example 2

Separation and Detection of Proteins by Capillary-Chip Electrophoresis Using DNA

[Target for Measurement (Antigen)]

Carcinoembryonic Antigen (CEA)(CosmoBio Co., Ltd.)

[Antibodies]

An anti-CEA antibody Fab' fragment to which had been bound DNA was prepared according to the same procedure as in Table 2 of Example 1, except that N-(ε-maleimidocaproyloxy)succinimide (EMCS) linker was used in place of the Sulfo-SMPB linker in the reaction in Table 2 of Example 1.

Briefly, 250 bp and 500 bp DNA fragments into which had been introduced an $NH_2$ group at the 5' end were purified in a conventional manner, and the $NH_2$ group introduced to these DNA fragments were allowed to react with the succinimido group of an N-(ε-maleimido-caproyloxy)succinimide (EMCS) linker (linker having a succinimido group and a maleimido group; Pierce chemical Co.) in a conventional manner. The product was applied to gel filtration to remove un-reacted linker yielding DNA fragments (250 bp and 500 bp) to which had been bound the linker, respectively. Thus resulting linker-binding 250 bp and 500 bp DNA fragments were allowed to react with an anti-CEA antibody WAC1 Fab' fragment which had been prepared from an anti-CEA antibody WAC1 (Wako Pure Chemical Industries, Ltd.) beforehand. In addition, the similarly prepared linker-binding 500 bp DNA fragment was allowed to react with a Fab' fragment which had been prepared from an anti-CEA antibody WAC2 (Wako Pure Chemical Industries, Ltd.). The respective products were purified with a DEAE column to give an anti-CEA antibody WAC1 Fab' fragment binding to the 250 bp DNA fragment (250 bpWAC1 antibody), an anti-CEA antibody WAC1 Fab' fragment binding to the 500 bp DNA fragment (500 bpWAC1 antibody) and an anti-CEA antibody WAC2 Fab' fragment binding to the 500 bp DNA fragment (500 bpWAC2 antibody), respectively.

[Samples]

A variety of specific antibodies were mixed and reacted with CEA at a specified concentration as described in Table 4 in an ACES buffer [50 mM N-(2-acetamido)-2-aminoethanesulfonic acid (ACES), pH 7.5] to use as samples as solutions.

In applying the samples to electrophoresis, as internal standards, a 50 bp double-strand DNA was added to the sample at 251 nM and/or a 10380 bp double-strand DNA was added at 0.61 nM. In addition, as controls, a 250 bp DNA fragment not binding to any antibody was added to the ample at 75 nM and/or a 500 bp DNA fragment was added at 45 nM. In this procedure, the internal standard and the control were mixed with the sample immediately before applying to electrophoresis.

TABLE 4

| Sample No. | 250bpWAC1 antibody 2.1 nM | 500bpWAC1 antibody 1.4 nM | 500bpWAC2 antibody 4.5 nM | CEA 300 nM |
|---|---|---|---|---|
| 1 | + | − | − | − |
| 2 | + | − | − | + |
| 3 | − | + | − | − |
| 4 | − | + | − | + |
| 5 | − | − | + | − |
| 6 | − | − | + | + |

[Electrophoretic Condition]

A capillary chip electrophoretic apparatus "Agilent 2100" (Agilent Technologies Inc.) was used as an electrophoretic apparatus. An analyzer "7500DNA Lab Chip™ kit" (Agilent Technologies Inc.) was used as an analyzer.

The analysis was conducted according to the instruction manual for use attached to the kit.

In this product, an intercalator dye is used as a marker in the gel packed in a capillary chip to carry out electrophoresis.

[Results]

Figure 16:
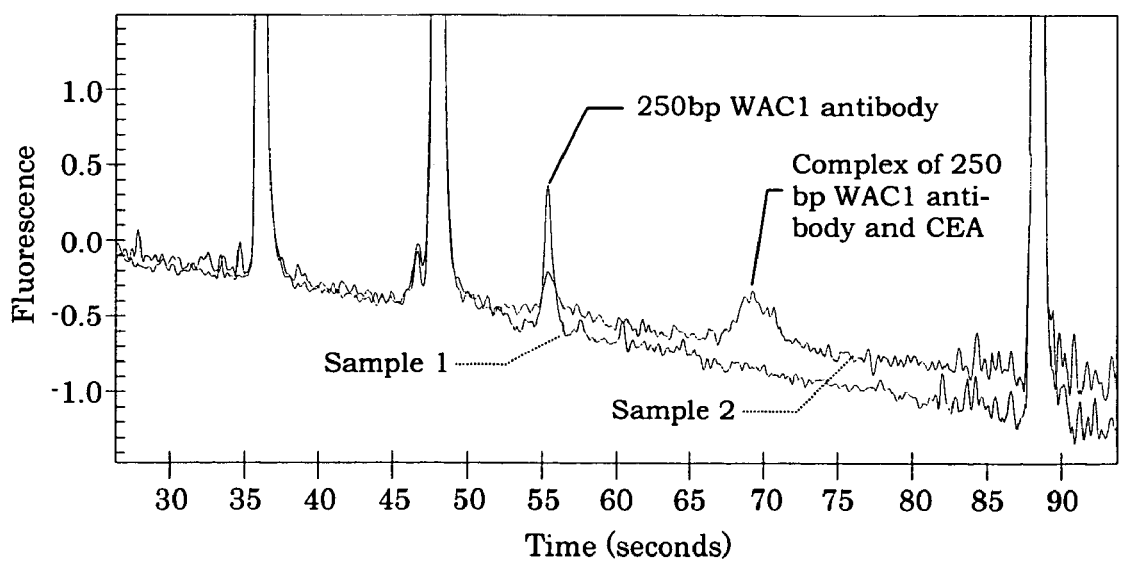
FIG. 16 shows a capillary chip electrophoretic chromatogram obtained by putting the result (capillary electrophoretic chromatogram) of electrophoresis for Sample 1 (containing 250 bpWAC1 antibody) on that (capillary electrophoretic chromatogram) for Sample 2 (containing a 250 bpWAC1 antibody-CEA complex) obtained in Example 2.
Figure 17:
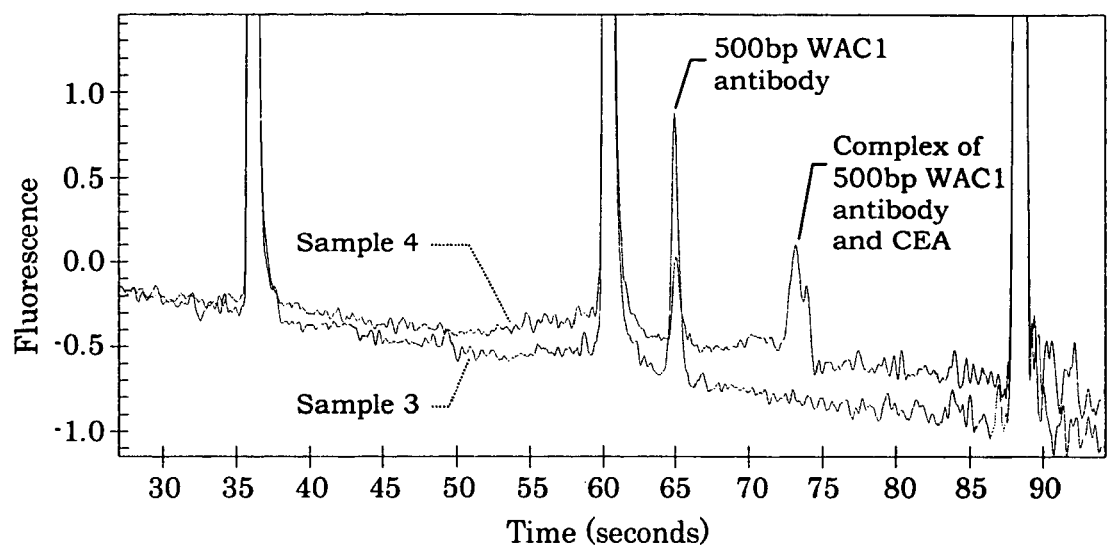
FIG. 17 shows a capillary chip electrophoretic chromatogram obtained by putting the result (capillary electrophoretic chromatogram) of electrophoresis for Sample 3 (containing 500 bpWAC1 antibody) on that (capillary electrophoretic chromatogram) for Sample 4 (containing a 500 bpWAC1 antibody-CEA complex) obtained in Example 2.
Figure 18:
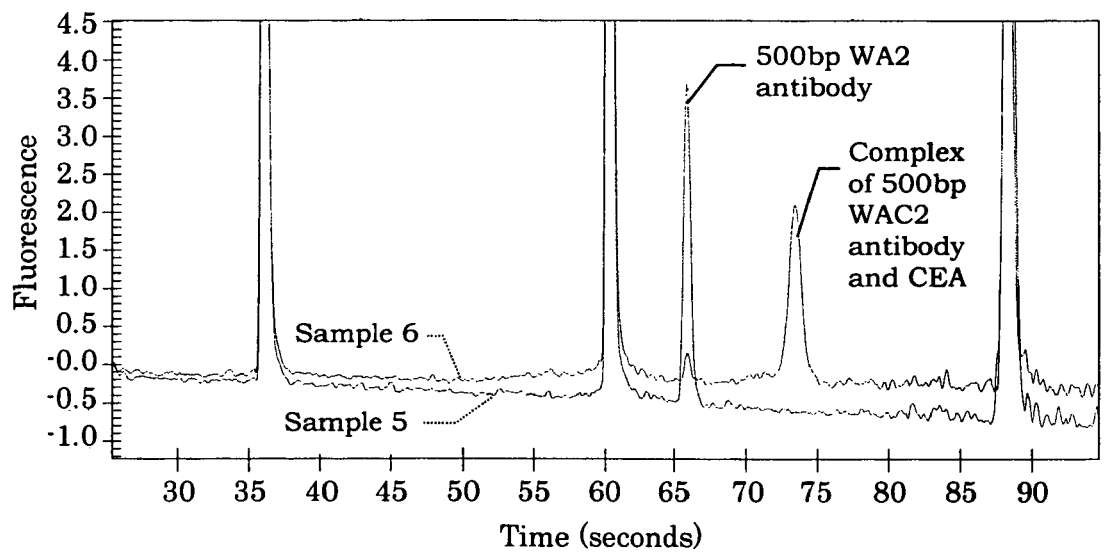
FIG. 18 shows a capillary chip electrophoretic chromatogram obtained by putting the result (capillary electrophoretic chromatogram) of electrophoresis for Sample 5 (containing 500 bpWAC2 antibody) on that (capillary electrophoretic chromatogram) for Sample 6 (containing a 500 bpWAC2 antibody-CEA complex) obtained in Example 2.

FIG. 16 shows a capillary chip electrophoretic chromatogram obtained by putting the result (capillary electrophoretic chromatogram) of electrophoresis for Sample 1 (containing 250 bpWAC1 antibody) on that (capillary electrophoretic chromatogram) for Sample 2 (containing a 250 bpWAC1 antibody-CEA complex). FIG. 17 shows a capillary chip electrophoretic chromatogram obtained by putting the result (capillary electrophoretic chromatogram) of electrophoresis for Sample 3 (containing 500 bpWAC1 antibody) on that (capillary electrophoretic chromatogram) for Sample 4 (containing a 500 bpWAC1 antibody-CEA complex). FIG. 18 shows a capillary chip electrophoretic chromatogram obtained by putting the result (capillary electrophoretic chromatogram) of electrophoresis for Sample 5 (containing 500 bpWAC2 antibody) on that (capillary electrophoretic chromatogram) for Sample 6 (containing a 500 bpWAC2 antibody-CEA complex).

From the results as shown in FIG. 16 to FIG. 18, it is understood that the binding of CEA to the antibody (formation of the complex) prolongs the retention time compared with that of the antibody alone. From the results as shown in FIG. 17 and FIG. 18, it is also understood that separation is possible similarly for different kinds of antibodies. Further, it is understandable from comparison with Example 1 that separation is also possible for different targets for measurement.

From the above facts, it is understood that, in the method of separation in the invention, formation of a complex comprising a target for measurement, a nucleic acid chain-binding affinity substance and a marker allows efficient separation of said complex from a complex of the nucleic acid chain-binding affinity substance and the marker not involved in the formation of said complex within a short period of time, said complex being formed by binding to the target for measurement a substance (nucleic acid chain-binding affinity substance) which has been linked to a nucleic acid chain labeled with a marker and has an affinity to the target for measurement.

Example 3

Separation and Detection of Proteins Depending on a Difference of Labeling Method

[Target for Measurement (Antigen)]
α-Fetoprotein (Wako Pure Chemical Industries, Ltd.)

[Antibodies]
Using an anti-AFP antibody A4-4 (Wako Pure Chemical Industries, Ltd.), respective labeled antibodies were prepared by different labeling methods as shown below.

Preparation of Cy5-Labeled Anti-AFP A4-4 Fab'

Using a primer 1 (ACTTTTTATATGAGGAGGGCTG) into which had been introduced a marker Cy5 at the 5' end and a primer 2 (ATCTATGACTGTACGCCACTGTCCCTAG) into which had been introduced a NH$_2$ group at the 5' end in a conventional manner, a PCR reaction was conducted on a λDNA as a template. Thus, a 160 bp DNA fragment which had Cy5 at one end and the NH$_2$ group at another end was prepared.

Using a 160 bp DNA fragment and the same reagents according to the procedure in Example 2, an anti-AFP antibody A4-4 Fab' fragment (Cy160A4-4 antibody) to which a 160 bp DNA fragment labeled with one molecule of Cy5 was bound through an EMCS linker was prepared.

Figure 19:
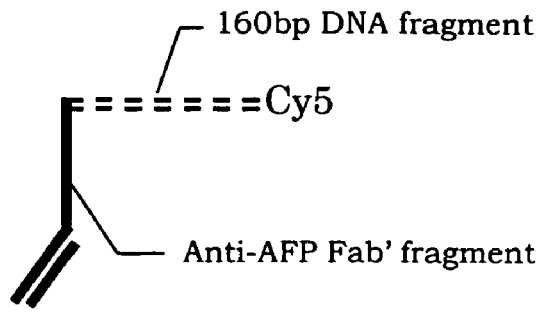
FIG. 19 schematically shows a labeling mode for the Cy160A4-4 antibody obtained in Example 3.

FIG. 19 schematically shows a labeling mode of the resulting Cy160A4-4 antibody.

Preparation of Cy5-Labeled Anti-AFPA4-4 Fab' Through Streptavidin

Using a primer 1 (ACTTTTTATATGAGGAGGGCTG) into which had been introduced biotin at the 5' end and a primer 2 (ATCTATGACTGTACGCCACTGTCCCTAG) into which had been introduced a NH$_2$ group at the 5' end in a conventional manner, a PCR reaction was conducted on a λDNA as a template. Thus, a 160 bp DNA fragment which had biotin at one end and the NH$_2$ group at another end was prepared.

Using this 160 bp DNA fragment and the same reagents according to the same procedure as in Example 2, an anti-AFP antibody A4-4 Fab' fragment (b-160A4-4 antibody) to which a 160 bp DNA fragment biotinylated at the end was bound through an EMCS linker was prepared.

In addition, an oligonucleotide was synthesized in a conventional manner. Using this oligonucleotide, a 21 bp DNA fragment (linker nucleic acid chain) (AATCTTC-CGAGTTTGCTAGGC) (Cy5-labeled 21 bp DNA fragment) which had biotin at the 5' end and was labeled with Cy5 at the 3' end was prepared.

Biotin-avidin reaction was carried out at a molecular ratio of b-160A4-4 antibody:Streptavidin=1:20. Removal of streptavidin remaining un-reacted using a Sepharose S-400 column (Amersham Pharmacia Biotech, Co.) afforded a streptavidin-binding b-160A4-4 antibody. Then, the streptavidin-binding b-160A4-4 antibody was allowed to react with 20 equimolar amount of the Cy5-labeled 21 bp DNA fragment and the reaction mixture was purified through a Sepharose S-400 column (Amersham Pharmacia Biotech, Co.) to give a streptavidin-binding b-160A4-4 antibody (Cy(3)160A4-4 antibody) into which was introduced 3 molecules of Cy5-labeled 21 bp DNA fragment.

Figure 20:
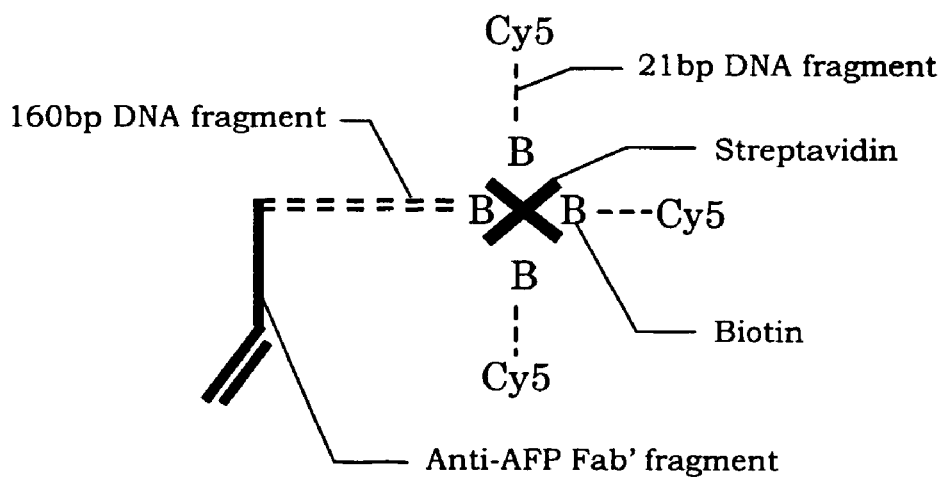
FIG. 20 schematically shows a labeling mode for the Cy(3) 160A4-4 antibody obtained in Example 3.

FIG. 20 schematically shows a labeling mode of the resulting Cy(3)160A4-4 antibody.

Preparation of Anti-AFPA4-4 Fab' to Which is Bound a Cy5-Labeled Streptavidin

Using a primer 3 (GCCTAGCAAACTCGGAAGATT) into which had been introduced biotin at the 5' end and a primer 2 (ATCTATGACTGTACGCCACTGTCCCTAG) into which had been introduced a $NH_2$ group at the 5' end in a conventional manner, a PCR reaction was conducted on a λDNA as a template. Thus, a 250 bp DNA fragment which had biotin at one end and the $NH_2$ group at another end was prepared.

Using this 250 bp DNA fragment and the same reagents according to the same procedure as in Example 2, an anti-AFP antibody A4-4 Fab' fragment to which a 250 bp DNA fragment biotinylated at the end (b-250A4-4 antibody) was bound through an EMCS linker was prepared.

In addition, streptavidin was labeled with Cy5 in a conventional manner using a FluoroLink™ Cy5 mono-functional dye kit (Amersham Pharmacia Biotech, Co.) according to the instruction manual for use attached to the kit to give a Cy5-labeled streptavidin.

Biotin-avidin reaction was carried out at a molecular ratio of b-250A4-4 antibody:Cy5-labeled streptavidin=1:20. The reaction mixture was purified using a Sepharose S-400 column (Amersham Pharmacia Biotech, Co.) to give a Cy5-labeled streptavidin-binding b-250A4-4 antibody (CySA250A4-4 antibody).

Figure 21:
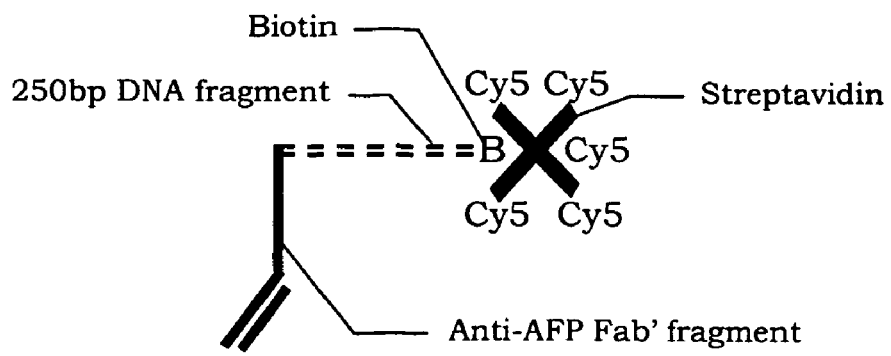
FIG. 21 schematically shows a labeling mode for the CySA250A4-4 antibody obtained in Example 3.

FIG. 21 schematically shows a labeling mode of the resulting CySA250A4-4 antibody.

[Samples]

A variety of specific antibodies were mixed and reacted with AFP at a specified concentration as described in Table 5 in an ACES buffer [50 mM N-(2-acetamido)-2-aminoethane-sulfonic acid (ACES), pH 7.5] to use as samples as solutions.

TABLE 5

| Sample No. | Cy160A4-4 antibody 10 nM | Cy(3) 160A4-4 antibody 10 nM | CySA250A4-4 antibody 10 nM | AFP 100 nM |
|---|---|---|---|---|
| 1 | + | − | − | − |
| 2 | + | − | − | + |
| 3 | − | + | − | − |
| 4 | − | + | − | + |
| 5 | − | − | + | − |
| 6 | − | − | + | + |

[Electrophoretic Condition]

A capillary chip electrophoretic apparatus "Agilent 2100" (Agilent Technologies Inc.) was used as an electrophoretic apparatus. An analyzer "7500DNA Lab Chip™ kit" (Agilent Technologies Inc.) was used as an analyzer.

The analysis was conducted according to the instruction manual for use attached to the kit.

In this example, an intercalator dye was not used as a mixture in the gel packed in a capillary chip to carry out electrophoresis.

[Results]

Figure 22:
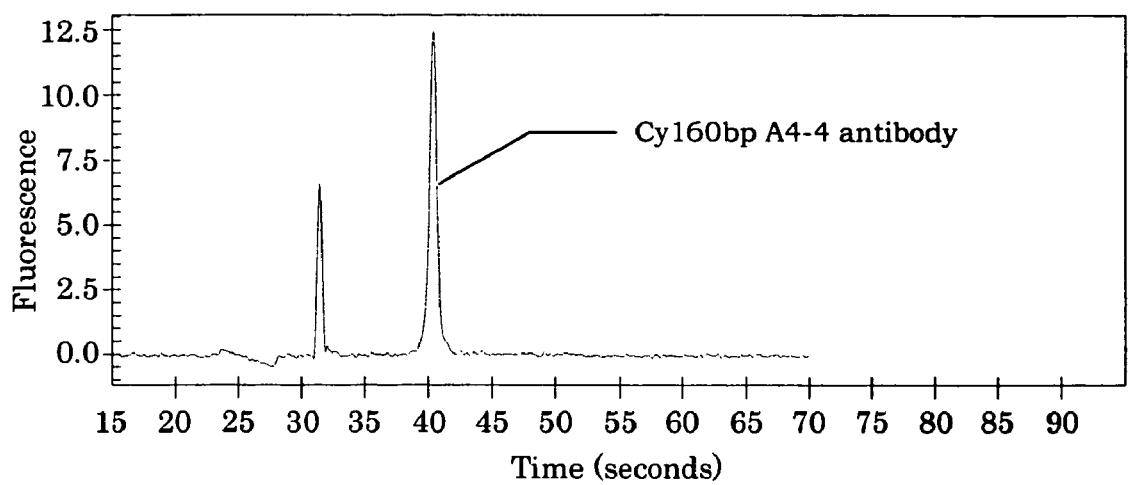
FIG. 22 shows the result (capillary chip electrophoretic chromatogram) of electrophoresis for Sample 1 (containing Cy160 bpA4-4 antibody) obtained in Example 3.
Figure 23:
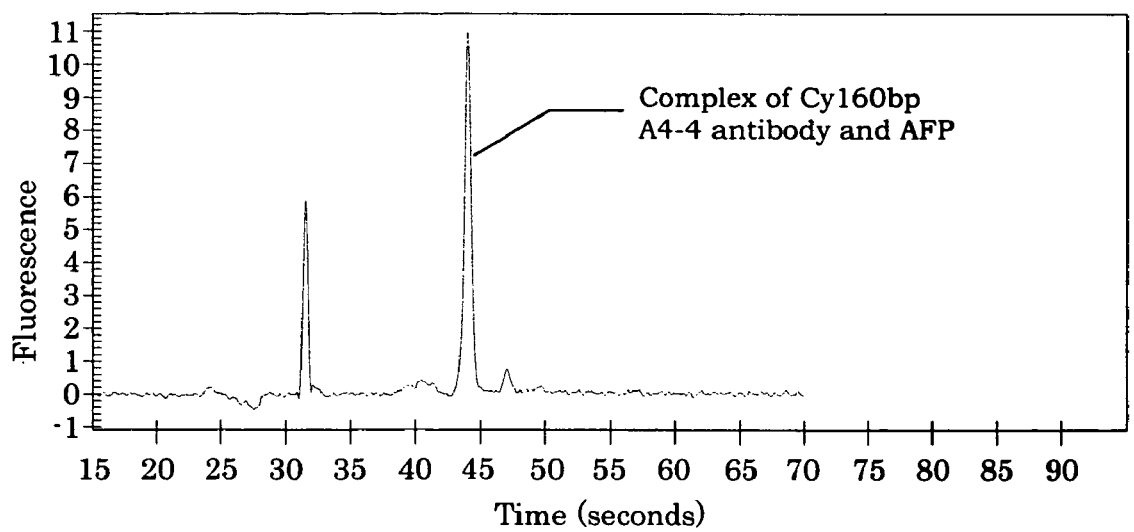
FIG. 23 shows the result (capillary chip electrophoretic chromatogram) of electrophoresis for Sample 2 (containing a Cy160 bpA4-4 antibody—AFP complex) obtained in Example 3.
Figure 24:
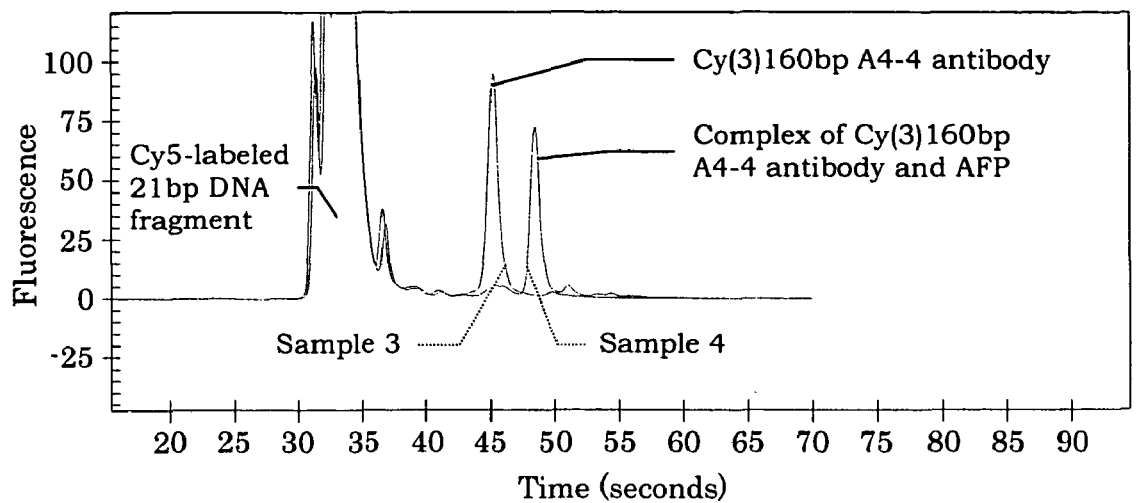
FIG. 24 shows a capillary chip electrophoretic chromatogram obtained by putting the result (capillary electrophoretic chromatogram) of electrophoresis for Sample 3 (containing Cy(3)160 bpA4-4 antibody) on that (capillary electrophoretic chromatogram) for Sample 4 (containing a Cy(3)160 bpA4-4 antibody-AFP complex) obtained in Example 3.
Figure 25:
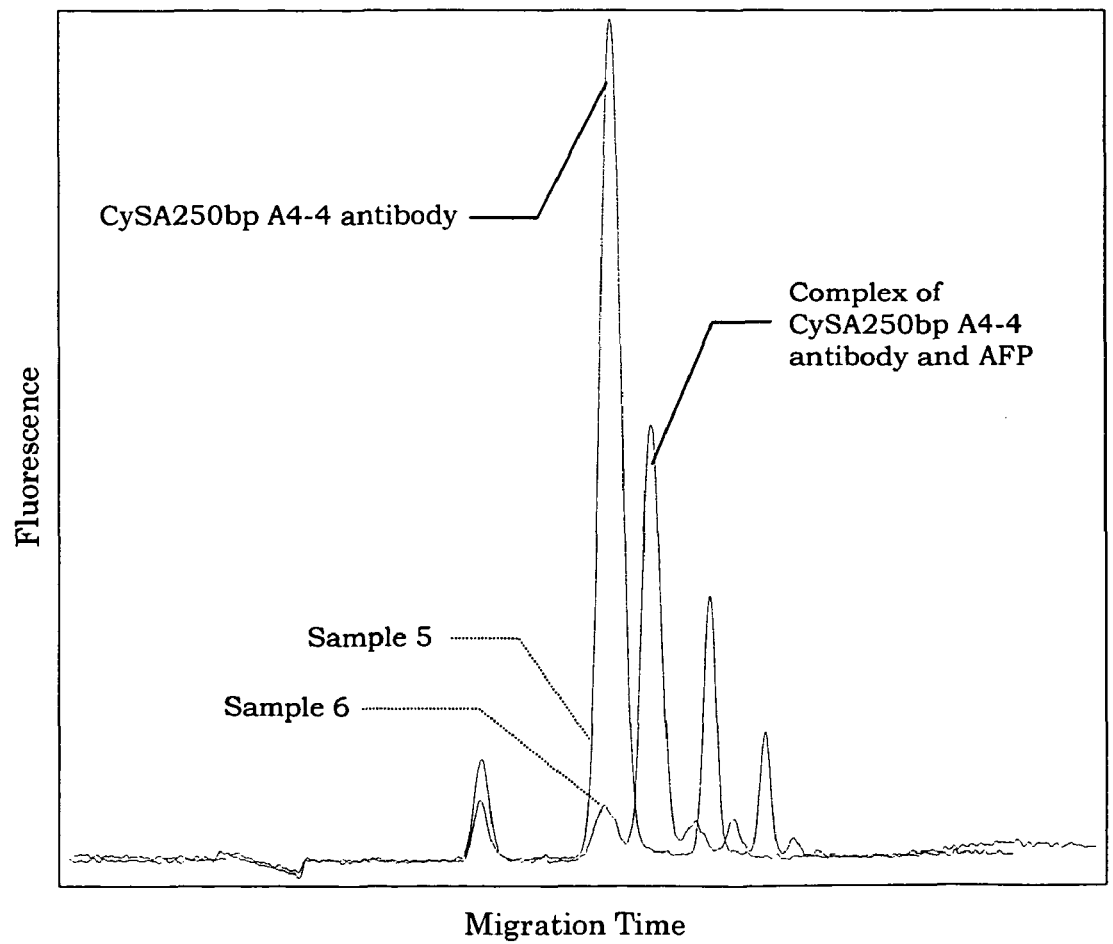
FIG. 25 shows a capillary chip electrophoretic chromatogram obtained by putting the result (capillary electrophoretic chromatogram) of electrophoresis for Sample 5 (containing CySA250 bpA4-4 antibody) on that (capillary electrophoretic chromatogram) for Sample 6 (containing a CySA250 bpA4-4 antibody-AFP complex) obtained in Example 3.

FIG. 22 shows the result (capillary electrophoretic chromatogram) of electrophoresis conducted for Sample 1 (containing Cy160 bpA4-4 antibody), and FIG. 23 shows the result (capillary electrophoretic chromatogram) of electrophoresis conducted for Sample 2 (containing a Cy160 bpA4-4 antibody-AFP complex). FIG. 24 shows a capillary chip electrophoretic chromatogram obtained by putting the result (capillary electrophoretic chromatogram) of electrophoresis for Sample 3 (containing Cy(3)160 bp A4-4 antibody) on that (capillary electrophoretic chromatogram) for Sample 4 (containing a Cy(3)160 bp A4-4 antibody-AFP complex). FIG. 25 shows a capillary chip electrophoretic chromatogram obtained by putting the result (capillary electrophoretic chromatogram) of electrophoresis for Sample 5 (containing CySA250 bpA4-4 antibody) on that (capillary electrophoretic chromatogram) for Sample 6 (containing a CySA250 bpA4-4 antibody-AFP complex).

From the results as shown in FIG. 22 and FIG. 23, it is understood that, when the nucleic acid chain is labeled directly with Cy5, the binding of AFP to the antibody (formation of the complex) prolongs the retention time compared with that of the antibody alone. From the results as shown in FIG. 24 and FIG. 25, it is also understood that, when a Cy5-labeled linker nucleic acid chain is bound to a nucleic acid chain through streptavidin (FIG. 24) or when a Cy5-labeled streptavidin is bound to a nucleic acid chain (FIG. 25), the binding of AFP to the antibody (formation of the complex) prolongs the retention time in either cases compared with that of the antibody alone.

This means that the separation is possible similarly even though the way of labeling of nucleic acid is different.

INDUSTRIAL APPLICABILITY

As mentioned above, the present invention provides a method for separating a target for measurement by electrophoresis, particularly capillary electrophoresis, efficiently in high sensitivity in a short period of time. According to the invention, a complex containing a target for measurement can be separated efficiently in a short period of time, and further a target for measurement contained in a sample can be determined in high sensitivity in a short period of time. Moreover, detection sensitivity can be controlled freely.

Up to now, there are some examples of separation of nucleic acids by capillary electrophoresis, but no example has been reported on satisfactory separation of native proteins. The reason is assumed that proteins composed of 20 kinds of amino acids have complicated steric structures compared with that of simple nucleic acids composed of 4 kinds of nucleotides and therefore no efficient molecular sieve effect can be attained for proteins.

In the invention, a target for measurement, for example, native protein, which was difficult to separate by a conventional electrophoresis, could successfully be separated first time efficiently in a short period of time. The invention is epoch-making, accordingly.

The invention claimed is:

1. A method for separation of a target for measurement which comprises using a complex-2 of i) a substance to which is bound a double-stranded nucleic acid chain and which has an affinity to the target and ii) a marker capable of labeling said double-stranded nucleic acid chain to form a complex-1 comprising a) the target, b) the substance and c) the marker, and separating said complex-1 from said complex-2 not involved in the formation of said complex-1 based on the difference of electrophoretic migration by electrophoresis.

2. The method as claimed in claim 1, wherein the method comprises:
   forming a complex-1 comprising a) the target, b) the substance and c) the marker from i) a sample containing the target, ii) the substance and iii) the marker, and
   separating said complex-1 from a complex-2 of the substance and the marker not involved in the formation of said complex-1 and if required from the marker based on the difference of electrophoretic migration by electrophoresis.

3. The method as claimed in claim 2, wherein the complex-1 is formed by mutually contacting the sample containing the target, the substance and the marker.

4. The method as claimed in claim 3, wherein the sample containing the target, the substance and the marker are made contact all at once.

5. The method as claimed in claim 3, wherein the marker is made contact with the substance, and then the product is made contact with the target for measurement.

6. The method as claimed in claim 3, wherein the substance is made contact with the target, and then the product is made contact with the marker.

7. A method for measurement of a target for measurement, which comprises measuring the complex-1 separated in the method as claimed in claim 2.

8. The method as claimed in claim 1, wherein the method comprises:
forming a complex-1 comprising a) the target, b) two or more species of the substances which have mutually different binding sites for the target for measurement each other, and c) the marker from i) a sample containing the target, ii) said two or more species of the substances and iii) the marker, and
separating said complex-1 from a complex-2 of the substance and the marker not involved in the formation of said complex-1 and if required from the marker based on the difference of electrophoretic migration by electrophoresis.

9. The method as claimed in claim 8, wherein the complex-1 is formed by mutually contacting the sample containing the target, said two or more species of the substances and the marker.

10. The method as claimed in claim 9, wherein the sample containing the target and said two or more species of the substances are made contact all at once.

11. The method as claimed in claim 9, wherein the marker is made contact with said two or more species of the substances, and then the product is made contact with the target for measurement.

12. The method as claimed in claim 9, wherein said two or more species of the substances are made contact with the target, and then the product is made contact with the marker.

13. A method for measurement of a target for measurement in a sample, which comprises measuring the complex-1 separated in the method as claimed in claim 8.

14. The method as claimed in claim 1, wherein the method comprises:
forming [1] a complex of a target $A_1$ for measurement among mutually different n types of targets $A_1$, $A_2$, $A_3$, ... $A_{n-1}$ and $A_n$ for measurement, a substance $B_{A1:An}$ to which is bound a double-stranded nucleic acid chain and which has an affinity to all of the targets $A_1$ to $A_n$, and the marker; [2] a complex of the target $A_2$, the substance $B_{A1:An}$, a substance $B_{A2:An}$ to which is bound a double-stranded nucleic acid chain and which has an affinity to all of the targets $A_1$ to $A_n$ except for $A_1$, and the marker; [3] a complex of the target $A_3$, the substance $B_{A1:An}$, the substance $B_{A2:An}$, a substance $B_{A3:An}$ to which is bound a double-stranded nucleic acid chain and which has an affinity to all of the targets $A_3$ to $A_n$ except for $A_1$ and $A_2$, and the marker; ... ; [n-1] a complex of the target $A_{n-1}$, the substance $B_{A1:An}$, the substance $B_{A2:An}$, the substance $B_{A3:An}$, ... and a substance $B_{An-1:An}$ to which is bound a double-stranded nucleic acid chain and which has an affinity to the targets $A_{n-1}$ and $A_n$ except for all of $A_1$ to $A_{n-2}$, and the marker; and [n] a complex of the target $A_n$, the substance $B_{A1:An}$, the substance $B_{A2:An}$, the substance $B_{A3:An}$, ... the substance $B_{An-1:An}$ and a substance $B_{An}$ to which is bound a double-stranded nucleic acid chain and which has an affinity only to the target $A_n$ except for all of $A_1$ to $A_{n-1}$, and the marker, from (a) a sample containing said mutually different n types of the targets $A_1$, $A_2$, $A_3$, ... $A_{n-1}$ and $A_n$, (b)(1) the substance $B_{A1:An}$, (2) the substance $B_{A2:An}$, (3) the substance $B_{A3:An}$, ... (n-1) the substance $B_{An-1:An}$, and (n) the substance $B_{An}$, and (c) the marker, and then
separating the respective complexes [1] to [n] from complexes of the respective substances (1) to (n) and the markers not involved in the formation of said complexes and if required from the markers based on the difference of electrophoretic migration by electrophoresis.

15. The method as claimed in claim 14, wherein n is 2 to 10.

16. The method as claimed in claim 14, wherein the complexes [1] to [n] are formed by mutually contacting (a) the sample containing said mutually different n types of targets $A_1$, $A_2$, $A_3$, $A_{n-1}$ and $A_n$, (b)(1) the substance $B_{A1:An}$, (2) the substance $B_{A2:An}$, (3) the substance $B_{A3:An}$, ..., (n-1) the substance $B_{An-1:An}$, and (n) the substance $B_{An}$, and (c) the marker.

17. The method as claimed in claim 16, wherein (a) the sample containing said mutually different n types of targets $A_1$, $A_2$, $A_3$, ... $A_{n-1}$ and $A_n$, (b)(1) the substance $B_{A1:An}$, (2) the substance $B_{A2:An}$, (3) the substance $B_{A3:An}$, ..., (n-1) the substance $B_{An-1:An}$, and (n) the substance $B_{An}$, and (c) the marker are made contact all at once.

18. The method as claimed in claim 16, wherein (b)(1) the substance $B_{A1:An}$, (2) the substance $B_{A2:An}$, (3) the substance $B_{A3:An}$, ..., (n-1) the substance $B_{An-1:An}$, and (n) the substance $B_{An}$ are made contact with (c) the marker, and then the product is made contact with (a) the sample containing said mutually different n types of targets $A_1$, $A_2$, $A_3$, ... $A_{n-1}$ and $A_n$.

19. The method as claimed in claim 16, wherein (a) the sample containing said mutually different n types of targets $A_1$, $A_2$, $A_3$, ... $A_{n-1}$ and $A_n$ is made contact with (b)(1) the substance $B_{A1:An}$, (2) the substance $B_{A2:An}$, (3) the substance $B_{A3:An}$, ..., (n-1) the substance $B_{An-1:An}$, and (n) the substance $B_{An}$, and then the product is made contact with (c) the marker.

20. A method for measurement of respective targets in a sample all at once, which comprises measuring respective complexes [1] to [n] separated in the method as claimed in claim 14.

21. The method as claimed in claim 1, wherein the method comprises:
forming 2 or more species of complex-1 comprising a) only one type of target among 2 or more types of targets for measurement, b) a substance to which is bound a double-stranded nucleic acid chain and which have an affinity only to said one type of target, and c) the marker capable of labeling said double-stranded nucleic acid chain, from i) a sample containing said 2 or more types of targets, ii) 2 or more species of substance, each of which is bound to a nucleic acid chain, and wherein each species of substance has an affinity only for any one of the intended targets, and iii) the marker, wherein each target is bound to at least one said substance to form said complex-1, and then
separating 2 or more species of complex-1 from each other and said complex-1 from a complex-2 of the substance and the marker not involved in the formation of said complex-1 and if required from the marker respectively based on the difference of electrophoretic migration by electrophoresis.

22. The method as claimed in claim 21, wherein the complex-1 is formed by mutually contacting the sample containing said 2 or more types of targets, said 2 or more species of substances, and the marker.

23. The method as claimed in claim 22, wherein the sample containing said 2 or more types of targets, said 2 or more species of substances, and the marker are made contact all at once.

24. The method as claimed in claim 22, wherein said 2 or more species of substances are made contact with the marker, and then the product is made contact with the sample containing said 2 or more types of the targets.

25. The method as claimed in claim 22, wherein the sample containing said 2 or more types of targets is made contact with said 2 or more species of substances, and then the product is made contact with the marker.

26. The method as claimed in claim 21, wherein each of said 2 or more types of the targets has the different number of the sites capable of binding to a substance having an affinity only therefor.

27. The method as claimed in claim 21, wherein the double-stranded nucleic acid chain binding to each of said 2 or more species of the substances is different in size.

28. A method for measurement of 2 or more types of targets for measurement in the sample all at once, which comprises measuring said 2 or more species of the complexes separated by the method as claimed in claim 21.

29. The method as claimed in claim 1, wherein the electrophoresis is capillary electrophoresis.

30. The method as claimed in claim 1, wherein said substance has a binding property for the target based on the interaction between proteins, between a protein and a chemical substance, or between chemical substances.

31. The method as claimed in claim 30, wherein said substance has a binding property for the target based on the interaction between antigen and antibody, sugar chain and lectin, enzyme and inhibitor, protein and peptide chain, or receptor and ligand.

32. A kit for measuring a target utilizing a separation based on the difference of electrophoretic migration by electrophoresis, comprising a substance to which is bound a double-stranded nucleic acid chain and which have an affinity for the target for measurement and a marker capable of labeling said double-stranded nucleic acid chain.

33. The kit as claimed in claim 32, further comprised of in combination with a capillary electrophoretic apparatus.

34. A kit for measuring a target utilizing a separation based on the difference of electrophoretic migration by electrophoresis, comprising a complex-2 of i) a substance to which is bound a double-stranded nucleic acid chain and which has affinity to the target for measurement and ii) a marker capable of labeling said double-stranded nucleic acid chain.

* * * * *